US009801913B2

(12) United States Patent
Ferraro et al.

(10) Patent No.: US 9,801,913 B2
(45) Date of Patent: *Oct. 31, 2017

(54) BARRIER LAYER

(75) Inventors: Joseph Ferraro, Londonderry, NH (US); Lisa Rogers, Londonderry, NH (US); Paul Martakos, Pelham, NH (US); Theodore Karwoski, Hollis, NH (US); Steve A. Herweck, Nashua, NH (US); Keith Faucher, Nashua, NH (US); Philip McNamara, Concord, NH (US)

(73) Assignee: ATRIUM MEDICAL CORPORATION, Hudson, NH (US)

( * ) Notice: Subject to any disclaimer, the term of this patent is extended or adjusted under 35 U.S.C. 154(b) by 725 days.

This patent is subject to a terminal disclaimer.

(21) Appl. No.: 11/237,420

(22) Filed: Sep. 28, 2005

(65) Prior Publication Data

US 2006/0078586 A1    Apr. 13, 2006

Related U.S. Application Data

(60) Provisional application No. 60/613,808, filed on Sep. 28, 2004.

(51) Int. Cl.

| | | |
|---|---|---|
| *A61K 35/60* | (2006.01) |
| *A61K 38/13* | (2006.01) |
| *A61L 27/36* | (2006.01) |
| *A61L 27/52* | (2006.01) |
| *A61K 9/00* | (2006.01) |
| *A61K 9/06* | (2006.01) |
| *A61K 31/225* | (2006.01) |
| *A61K 31/355* | (2006.01) |
| *A61K 47/12* | (2006.01) |
| *A61K 47/14* | (2017.01) |
| *A61L 31/10* | (2006.01) |
| *A61L 27/54* | (2006.01) |
| *A61F 13/02* | (2006.01) |
| *A61L 2/07* | (2006.01) |
| *A61L 2/08* | (2006.01) |
| *A61L 2/20* | (2006.01) |
| *A61L 31/00* | (2006.01) |
| *A61L 31/14* | (2006.01) |
| *A61F 2/06* | (2013.01) |
| *B05D 3/06* | (2006.01) |

(52) U.S. Cl.
CPC .............. *A61K 35/60* (2013.01); *A61F 13/02* (2013.01); *A61F 13/023* (2013.01); *A61K 9/0024* (2013.01); *A61K 9/06* (2013.01); *A61K 31/225* (2013.01); *A61K 31/355* (2013.01); *A61K 38/13* (2013.01); *A61K 47/12* (2013.01); *A61K 47/14* (2013.01); *A61L 2/07* (2013.01); *A61L 2/081* (2013.01); *A61L 2/087* (2013.01); *A61L 2/206* (2013.01); *A61L 2/208* (2013.01); *A61L 27/36* (2013.01); *A61L 27/3604* (2013.01); *A61L 27/52* (2013.01); *A61L 27/54* (2013.01); *A61L 31/005* (2013.01); *A61L 31/10* (2013.01); *A61L 31/145* (2013.01); *A61F 2/06* (2013.01); *A61F 2250/0067* (2013.01); *A61L 2202/24* (2013.01); *A61L 2300/22* (2013.01); *A61L 2300/252* (2013.01); *A61L 2300/404* (2013.01); *A61L 2300/41* (2013.01); *A61L 2300/414* (2013.01); *A61L 2300/42* (2013.01); *A61L 2300/602* (2013.01); *B05D 3/067* (2013.01)

(58) Field of Classification Search
None
See application file for complete search history.

(56) References Cited

U.S. PATENT DOCUMENTS

| | | | | |
|---|---|---|---|---|
| 1,948,959 | A | * | 2/1934 | Croce ........................... 106/222 |
| 2,368,306 | A | | 1/1945 | Kiefer et al. |
| 2,403,458 | A | * | 7/1946 | Ransom et al. .............. 554/206 |
| 2,735,814 | A | | 2/1956 | Hodson et al. |
| 2,986,540 | A | | 5/1961 | Posnansky |
| 3,464,413 | A | | 9/1969 | Goldfarb et al. |
| 3,556,294 | A | | 1/1971 | Walck et al. |

(Continued)

FOREIGN PATENT DOCUMENTS

| | | | | |
|---|---|---|---|---|
| EP | 0471566 | | 2/1992 | |
| EP | 610731 | A1 * | 8/1994 | ............. A61L 31/00 |

(Continued)

OTHER PUBLICATIONS

Cure in Academic Press Dictionary of Science and Technology 1992.*
Ahuja et al. Journal of Indian Pediatric Surgery 2002 7:15-20.*
Morse Industrial and Engineering Chemistry 1941 33:1039-1043.*
Mallegol et al. Progress in Organic Coatings 2000 39:107-113.*
Timar-Balzsy et al. Chemical Principles of Textile Conservation. Oxford: Elsevier Science Ltd., 1998. 117-119.*
Mallegol et al. Journal of the American Oil Chemists' Society 2000 77:257-263.*
Wicks et al. Organic Coatings:Science and Technology 1999 New York:Wiley Interscience p. 258-267.*
Mills et al. Oils and Fats. "The Organic Chemistry of Museum Objects" London:Buttersworth and Co. 1987, p. 26-40.*
Erhardt Paints Based on Drying Oil Media. Painted Wood: History & Conservation. Ed. Berland Singapore: The J. Paul Getty Trust 1998. p. 17-32.*
Wexler et al. Chemical Reviews 1964 64(6):591-611.*
Polymer—The Chambers 21st Century Dictionary M. Robinson and G. Davidson (Eds.), London, United Kingdom: Chambers Harrap. Retrieved from http://search.credoreference.com/content/entry/chambdict/polymer/0.*

(Continued)

*Primary Examiner* — Robert A Wax
*Assistant Examiner* — Caralynne Helm
(74) *Attorney, Agent, or Firm* — Wesley Scott Ashton

(57) ABSTRACT

A barrier layer and corresponding method of making provide anti-inflammatory, non-inflammatory, and anti-adhesion functionality for a medical device implantable in a patient. The barrier layer can be combined with a medical device structure to provide anti-adhesion characteristics, in addition to improved healing, non-inflammatory, and anti-inflammatory response. The barrier layer is generally formed of a naturally occurring oil, or an oil composition formed in part of a naturally occurring oil, that is at least partially cured forming a cross-linked gel. In addition, the oil composition can include a therapeutic agent component, such as a drug or other bioactive agent.

26 Claims, 7 Drawing Sheets

(56) References Cited

U.S. PATENT DOCUMENTS

| | | |
|---|---|---|
| 3,567,820 A | 3/1971 | Sperti |
| 3,803,109 A | 4/1974 | Nemoto et al. |
| 3,967,728 A | 7/1976 | Gordon et al. |
| 4,308,120 A | 12/1981 | Pennewiss et al. |
| 4,323,547 A | 4/1982 | Knust et al. |
| 4,447,418 A | 5/1984 | Maddoux |
| 4,557,925 A | 12/1985 | Lindahl et al. |
| 4,664,114 A | 5/1987 | Ghodsian |
| 4,813,210 A | 3/1989 | Masuda et al. |
| 4,814,329 A | 3/1989 | Harsanyi et al. |
| 4,847,301 A | 7/1989 | Murray |
| 4,880,455 A | 11/1989 | Blank |
| 4,883,667 A | 11/1989 | Eckenhoff |
| 4,886,787 A | 12/1989 | De Belder et al. |
| 4,894,231 A | 1/1990 | Moreau et al. |
| 4,895,724 A | 1/1990 | Cardinal et al. |
| 4,911,707 A | 3/1990 | Heiber et al. |
| 4,937,254 A | 6/1990 | Sheffield et al. |
| 4,938,763 A | 7/1990 | Dunn et al. |
| 4,941,308 A | 7/1990 | Grabenkort et al. |
| 4,952,419 A | 8/1990 | De Leon |
| 4,968,302 A | 11/1990 | Schluter et al. |
| 5,017,229 A | 5/1991 | Burns et al. |
| 5,132,115 A | 7/1992 | Wolter et al. |
| 5,147,374 A | 9/1992 | Fernandez |
| 5,151,272 A | 9/1992 | Engstrom et al. |
| 5,171,148 A | 12/1992 | Wasserman et al. |
| 5,176,956 A | 1/1993 | Jevne et al. |
| 5,179,174 A | 1/1993 | Elton |
| 5,202,310 A | 4/1993 | Levy et al. |
| 5,254,105 A | 10/1993 | Haaga |
| 5,356,432 A | 10/1994 | Rutkow et al. |
| 5,368,602 A | 11/1994 | de la Torre |
| 5,371,109 A | 12/1994 | Engstrom et al. |
| 5,380,328 A | 1/1995 | Morgan |
| 5,387,658 A * | 2/1995 | Schroder et al. ............. 525/530 |
| 5,403,283 A | 4/1995 | Luther |
| 5,411,951 A | 5/1995 | Mitchell |
| 5,411,988 A | 5/1995 | Bockow et al. |
| 5,447,940 A * | 9/1995 | Harvey et al. ................ 514/310 |
| 5,464,650 A | 11/1995 | Berg et al. |
| 5,480,653 A | 1/1996 | Aguadisch et al. |
| 5,509,899 A | 4/1996 | Fan et al. |
| 5,547,677 A | 8/1996 | Wright |
| 5,549,901 A | 8/1996 | Wright |
| 5,579,149 A | 11/1996 | Moret et al. |
| 5,580,923 A | 12/1996 | Yeung et al. |
| 5,589,508 A | 12/1996 | Schlotzer et al. |
| 5,591,230 A | 1/1997 | Horn et al. |
| 5,593,441 A * | 1/1997 | Lichtenstein et al. ......... 600/37 |
| 5,612,074 A | 3/1997 | Leach |
| 5,614,284 A | 3/1997 | Kranzler et al. |
| 5,627,077 A | 5/1997 | Dyllick-Brenzinger et al. |
| 5,629,021 A | 5/1997 | Wright |
| 5,637,113 A | 6/1997 | Tartaglia et al. |
| 5,665,115 A | 9/1997 | Cragg |
| 5,695,525 A | 12/1997 | Mulhauser et al. |
| 5,700,286 A | 12/1997 | Tartaglia et al. |
| 5,731,346 A | 3/1998 | Egberg et al. |
| 5,736,152 A | 4/1998 | Dunn |
| 5,747,533 A | 5/1998 | Egberg et al. |
| 5,753,259 A | 5/1998 | Engstrom et al. |
| 5,760,081 A | 6/1998 | Leaf et al. |
| 5,766,246 A | 6/1998 | Mulhauser et al. |
| 5,766,710 A | 6/1998 | Turnlund et al. |
| 5,789,465 A | 8/1998 | Harvey et al. |
| 5,817,343 A | 10/1998 | Burke |
| 5,824,082 A | 10/1998 | Brown |
| 5,837,313 A | 11/1998 | Ding et al. |
| 5,843,919 A | 12/1998 | Burger |
| 5,874,470 A | 2/1999 | Nehne et al. |
| 5,879,359 A | 3/1999 | Dorigatti et al. |
| 5,898,040 A | 4/1999 | Shalaby et al. |
| 5,906,831 A | 5/1999 | Larsson et al. |
| 5,931,165 A | 8/1999 | Reich et al. |
| 5,955,502 A | 9/1999 | Hansen et al. |
| 5,986,043 A | 11/1999 | Hubbell et al. |
| 6,005,004 A | 12/1999 | Katz et al. |
| 6,010,766 A | 1/2000 | Braun et al. |
| 6,010,776 A | 1/2000 | Exsted et al. |
| 6,015,844 A | 1/2000 | Harvey et al. |
| 6,028,164 A | 2/2000 | Loomis |
| 6,040,330 A | 3/2000 | Hausheer et al. |
| 6,048,725 A | 4/2000 | Shimada et al. |
| 6,056,970 A | 5/2000 | Greenawalt et al. |
| 6,077,698 A | 6/2000 | Swan et al. |
| 6,080,442 A | 6/2000 | Yoshikawa et al. |
| 6,083,950 A | 7/2000 | Anand et al. |
| 6,090,809 A | 7/2000 | Anand et al. |
| 6,093,792 A | 7/2000 | Gross et al. |
| 6,117,911 A | 9/2000 | Grainger et al. |
| 6,120,539 A | 9/2000 | Eldridge et al. |
| 6,120,789 A | 9/2000 | Dunn |
| 6,132,765 A | 10/2000 | DiCosmo et al. |
| 6,146,358 A | 11/2000 | Rowe |
| 6,152,944 A | 11/2000 | Holman et al. |
| 6,176,863 B1 | 1/2001 | Kugel et al. |
| 6,193,746 B1 | 2/2001 | Strecker |
| 6,197,357 B1 | 3/2001 | Lawton et al. |
| 6,203,551 B1 | 3/2001 | Wu |
| 6,206,916 B1 | 3/2001 | Furst |
| 6,211,315 B1 | 4/2001 | Larock et al. |
| 6,228,383 B1 | 5/2001 | Hansen et al. |
| 6,229,032 B1 | 5/2001 | Jacobs et al. |
| 6,245,366 B1 | 6/2001 | Popplewell et al. |
| 6,245,811 B1 | 6/2001 | Horrobin et al. |
| 6,254,634 B1 | 7/2001 | Anderson et al. |
| 6,262,109 B1 | 7/2001 | Clark et al. |
| 6,273,913 B1 | 8/2001 | Wright et al. |
| 6,284,268 B1 | 9/2001 | Mishra et al. |
| 6,299,604 B1 | 10/2001 | Ragheb et al. |
| 6,326,360 B1 | 12/2001 | Kanazawa et al. |
| 6,331,568 B1 | 12/2001 | Horrobin |
| 6,342,254 B1 | 1/2002 | Soudant et al. |
| 6,346,110 B2 | 2/2002 | Wu |
| 6,358,556 B1 | 3/2002 | Ding et al. |
| 6,364,893 B1 | 4/2002 | Sahatjian et al. |
| 6,368,658 B1 | 4/2002 | Schwarz et al. |
| 6,369,039 B1 | 4/2002 | Palasis et al. |
| 6,387,379 B1 | 5/2002 | Goldberg et al. |
| 6,410,587 B1 | 6/2002 | Grainger et al. |
| 6,444,318 B1 | 9/2002 | Guire et al. |
| 6,451,373 B1 | 9/2002 | Hossainy et al. |
| 6,465,525 B1 | 10/2002 | Guire et al. |
| 6,471,980 B2 | 10/2002 | Sirhan et al. |
| 6,479,683 B1 | 11/2002 | Abney et al. |
| 6,485,752 B1 | 11/2002 | Rein et al. |
| 6,491,938 B2 | 12/2002 | Kunz et al. |
| 6,500,453 B2 | 12/2002 | Brey et al. |
| 6,503,556 B2 | 1/2003 | Harish et al. |
| 6,525,145 B2 | 2/2003 | Gevaert et al. |
| 6,527,801 B1 | 3/2003 | Dutta |
| 6,534,693 B2 | 3/2003 | Fischell et al. |
| 6,548,081 B2 * | 4/2003 | Sadozai et al. ................ 424/426 |
| 6,565,659 B1 | 5/2003 | Pacetti et al. |
| 6,569,441 B2 | 5/2003 | Kunz et al. |
| 6,599,323 B2 | 7/2003 | Melican et al. |
| 6,610,035 B2 | 8/2003 | Yang et al. |
| 6,610,068 B1 | 8/2003 | Yang et al. |
| 6,630,151 B1 | 10/2003 | Tarletsky et al. |
| 6,630,167 B2 | 10/2003 | Zhang |
| 6,632,822 B1 | 10/2003 | Rickards et al. |
| 6,641,611 B2 | 11/2003 | Jayaraman |
| 6,645,547 B1 | 11/2003 | Shekalim |
| 6,663,880 B1 | 12/2003 | Roorda et al. |
| 6,669,735 B1 | 12/2003 | Pelissier |
| 6,670,355 B2 | 12/2003 | Azrolan et al. |
| 6,677,342 B2 | 1/2004 | Wolff et al. |
| 6,677,386 B1 | 1/2004 | Giezen et al. |
| 6,685,956 B2 | 2/2004 | Chu et al. |
| 6,696,583 B2 | 2/2004 | Koncar et al. |
| 6,730,064 B2 | 5/2004 | Ragheb et al. |
| 6,753,071 B1 | 6/2004 | Pacetti |
| 6,761,903 B2 | 7/2004 | Chen et al. |

(56) References Cited

U.S. PATENT DOCUMENTS

| | | | |
|---|---|---|---|
| 6,764,509 B2 | 7/2004 | Chinn et al. | |
| 6,776,796 B2 | 8/2004 | Falotico et al. | |
| 6,794,485 B2 | 9/2004 | Shalaby et al. | |
| 6,833,004 B2 | 12/2004 | Ishii et al. | |
| 6,852,330 B2 | 2/2005 | Bowman et al. | |
| 6,875,230 B1 | 4/2005 | Morita et al. | |
| 6,884,428 B2 | 4/2005 | Binette et al. | |
| 6,887,270 B2 | 5/2005 | Miller et al. | |
| 6,899,729 B1 | 5/2005 | Cox et al. | |
| 6,918,927 B2 | 7/2005 | Bates et al. | |
| 6,996,952 B2 | 2/2006 | Gupta et al. | |
| 7,070,858 B2 | 7/2006 | Shalaby et al. | |
| 7,101,381 B2 | 9/2006 | Ford et al. | |
| 7,152,611 B2 | 12/2006 | Brown et al. | |
| 7,323,189 B2 * | 1/2008 | Pathak | 424/423 |
| 7,415,811 B2 | 8/2008 | Gottlieb et al. | |
| 7,854,958 B2 | 12/2010 | Kramer | |
| 7,947,015 B2 | 5/2011 | Herweck et al. | |
| 8,124,127 B2 | 2/2012 | Faucher et al. | |
| 8,263,102 B2 | 9/2012 | Labrecque et al. | |
| 8,308,684 B2 | 11/2012 | Herweck et al. | |
| 8,312,836 B2 | 11/2012 | Corbeil et al. | |
| 8,367,099 B2 | 2/2013 | Herweck et al. | |
| 8,501,229 B2 | 8/2013 | Faucher et al. | |
| 8,722,077 B2 | 5/2014 | Labrecque et al. | |
| 9,000,040 B2 | 4/2015 | Faucher et al. | |
| 9,012,506 B2 | 4/2015 | Faucher et al. | |
| 2001/0025034 A1 | 9/2001 | Arbiser | |
| 2001/0025196 A1 | 9/2001 | Chinn et al. | |
| 2001/0051595 A1 | 12/2001 | Lyons et al. | |
| 2002/0002154 A1 | 1/2002 | Guivarc'h et al. | |
| 2002/0007209 A1 | 1/2002 | Scheerder et al. | |
| 2002/0012741 A1 | 1/2002 | Heinz et al. | |
| 2002/0026899 A1 | 3/2002 | McLaughlin et al. | |
| 2002/0026900 A1 | 3/2002 | Huang et al. | |
| 2002/0032414 A1 | 3/2002 | Ragheb et al. | |
| 2002/0055701 A1 | 5/2002 | Fischell et al. | |
| 2002/0098278 A1 | 7/2002 | Bates et al. | |
| 2002/0116045 A1 | 8/2002 | Eidenschink | |
| 2002/0120333 A1 | 8/2002 | Keogh et al. | |
| 2002/0122877 A1 | 9/2002 | Harish et al. | |
| 2002/0142089 A1 | 10/2002 | Koike et al. | |
| 2002/0193829 A1 | 12/2002 | Kennedy et al. | |
| 2003/0003125 A1 | 1/2003 | Nathan et al. | |
| 2003/0003221 A1 | 1/2003 | Zhong et al. | |
| 2003/0004564 A1 | 1/2003 | Elkins et al. | |
| 2003/0009213 A1 | 1/2003 | Yang | |
| 2003/0055403 A1 | 3/2003 | Nestenborg et al. | |
| 2003/0065292 A1 | 4/2003 | Darouiche et al. | |
| 2003/0065345 A1 | 4/2003 | Weadock | |
| 2003/0069632 A1 | 4/2003 | De Scheerder et al. | |
| 2003/0072784 A1 | 4/2003 | Williams | |
| 2003/0077272 A1 | 4/2003 | Pathak | |
| 2003/0077310 A1 | 4/2003 | Pathak et al. | |
| 2003/0077452 A1 | 4/2003 | Guire et al. | |
| 2003/0083740 A1 | 5/2003 | Pathak | |
| 2003/0086958 A1 | 5/2003 | Arnold et al. | |
| 2003/0094728 A1 | 5/2003 | Tayebi | |
| 2003/0108588 A1 | 6/2003 | Chen et al. | |
| 2003/0130206 A1 | 7/2003 | Koziak et al. | |
| 2003/0152609 A1 | 8/2003 | Fischell et al. | |
| 2003/0175408 A1 | 9/2003 | Timm et al. | |
| 2003/0176915 A1 | 9/2003 | Wright et al. | |
| 2003/0181975 A1 | 9/2003 | Ishii et al. | |
| 2003/0191179 A1 | 10/2003 | Joshi-Hangal et al. | |
| 2003/0204168 A1 | 10/2003 | Bosma et al. | |
| 2003/0204618 A1 | 10/2003 | Foster et al. | |
| 2003/0207019 A1 | 11/2003 | Shekalim et al. | |
| 2003/0211230 A1 | 11/2003 | Pacetti et al. | |
| 2003/0220297 A1 | 11/2003 | Berstein et al. | |
| 2004/0006296 A1 | 1/2004 | Fischell et al. | |
| 2004/0014810 A1 | 1/2004 | Horrobin | |
| 2004/0018228 A1 | 1/2004 | Fischell et al. | |
| 2004/0039441 A1 | 2/2004 | Rowland et al. | |
| 2004/0060260 A1 | 4/2004 | Gottlieb et al. | |
| 2004/0071756 A1 | 4/2004 | Fischell et al. | |
| 2004/0072849 A1 | 4/2004 | Schreiber et al. | |
| 2004/0073284 A1 | 4/2004 | Bates et al. | |
| 2004/0117007 A1 | 6/2004 | Whitbourne et al. | |
| 2004/0131755 A1 | 7/2004 | Zhong et al. | |
| 2004/0133275 A1 | 7/2004 | Mansmann | |
| 2004/0137066 A1 | 7/2004 | Jayaraman | |
| 2004/0137179 A1 | 7/2004 | Matsuda et al. | |
| 2004/0142094 A1 | 7/2004 | Narayanan | |
| 2004/0146546 A1 * | 7/2004 | Gravett et al. | 424/445 |
| 2004/0156879 A1 | 8/2004 | Muratoglu et al. | |
| 2004/0161464 A1 | 8/2004 | Domb | |
| 2004/0167572 A1 | 8/2004 | Roth et al. | |
| 2004/0170685 A1 | 9/2004 | Carpenter et al. | |
| 2004/0192643 A1 | 9/2004 | Pressato et al. | |
| 2004/0215219 A1 | 10/2004 | Eldridge et al. | |
| 2004/0224003 A1 * | 11/2004 | Schultz | 424/423 |
| 2004/0230176 A1 | 11/2004 | Shanahan et al. | |
| 2004/0234574 A9 | 11/2004 | Sawhney et al. | |
| 2004/0241211 A9 | 12/2004 | Fischell | |
| 2004/0256264 A1 | 12/2004 | Israelsson et al. | |
| 2005/0010078 A1 | 1/2005 | Jamiolkowski et al. | |
| 2005/0084514 A1 | 4/2005 | Shebuski et al. | |
| 2005/0095267 A1 | 5/2005 | Campbell et al. | |
| 2005/0100655 A1 | 5/2005 | Zhong et al. | |
| 2005/0106209 A1 | 5/2005 | Ameri et al. | |
| 2005/0112170 A1 | 5/2005 | Hossainy et al. | |
| 2005/0113849 A1 | 5/2005 | Popadiuk et al. | |
| 2005/0124062 A1 | 6/2005 | Subirade | |
| 2005/0129787 A1 | 6/2005 | Murad | |
| 2005/0158361 A1 * | 7/2005 | Dhondt et al. | 424/425 |
| 2005/0159809 A1 | 7/2005 | Hezi-Yamit et al. | |
| 2005/0165476 A1 | 7/2005 | Furst et al. | |
| 2005/0165477 A1 | 7/2005 | Anduiza et al. | |
| 2005/0182485 A1 | 8/2005 | Falotico et al. | |
| 2005/0187376 A1 | 8/2005 | Pacetti | |
| 2005/0203635 A1 | 9/2005 | Hunter et al. | |
| 2005/0203636 A1 | 9/2005 | McFetridge | |
| 2005/0223679 A1 | 10/2005 | Gottlieb et al. | |
| 2005/0232971 A1 | 10/2005 | Hossainy et al. | |
| 2005/0249775 A1 | 11/2005 | Falotico et al. | |
| 2005/0283229 A1 | 12/2005 | Dugan et al. | |
| 2006/0008501 A1 | 1/2006 | Dhont et al. | |
| 2006/0036311 A1 | 2/2006 | Nakayama et al. | |
| 2006/0051544 A1 * | 3/2006 | Goldmann | 428/35.8 |
| 2006/0058881 A1 | 3/2006 | Trieu | |
| 2006/0067974 A1 | 3/2006 | Labrecque et al. | |
| 2006/0067975 A1 | 3/2006 | Labrecque et al. | |
| 2006/0067976 A1 | 3/2006 | Ferraro et al. | |
| 2006/0067977 A1 | 3/2006 | Labrecque et al. | |
| 2006/0067983 A1 | 3/2006 | Swanick et al. | |
| 2006/0068674 A1 | 3/2006 | Dixit et al. | |
| 2006/0078586 A1 | 4/2006 | Ferraro et al. | |
| 2006/0083768 A1 | 4/2006 | Labrecque et al. | |
| 2006/0088596 A1 | 4/2006 | Labrecque et al. | |
| 2006/0093643 A1 | 5/2006 | Stenzel | |
| 2006/0110457 A1 | 5/2006 | Labrecque et al. | |
| 2006/0121081 A1 | 6/2006 | Labrecque et al. | |
| 2006/0124056 A1 | 6/2006 | Behnisch et al. | |
| 2006/0134209 A1 | 6/2006 | Labhasetwar et al. | |
| 2006/0158361 A1 | 7/2006 | Chou | |
| 2006/0188607 A1 | 8/2006 | Schramm et al. | |
| 2006/0204738 A1 | 9/2006 | Dubrow et al. | |
| 2006/0210701 A1 | 9/2006 | Chappa et al. | |
| 2006/0240069 A1 | 10/2006 | Utas et al. | |
| 2006/0246105 A1 | 11/2006 | Molz et al. | |
| 2007/0015893 A1 | 1/2007 | Hakuta et al. | |
| 2007/0071798 A1 | 3/2007 | Herweck et al. | |
| 2007/0084144 A1 | 4/2007 | Labrecque et al. | |
| 2007/0093894 A1 | 4/2007 | Darouiche | |
| 2007/0141112 A1 | 6/2007 | Falotico et al. | |
| 2007/0202149 A1 | 8/2007 | Faucher et al. | |
| 2007/0212411 A1 | 9/2007 | Fawzy et al. | |
| 2007/0264460 A1 | 11/2007 | Del Tredici | |
| 2007/0275074 A1 | 11/2007 | Holm et al. | |
| 2007/0280986 A1 | 12/2007 | Gil et al. | |
| 2007/0286891 A1 | 12/2007 | Kettlewell et al. | |
| 2007/0299538 A1 | 12/2007 | Roeber | |
| 2008/0038307 A1 | 2/2008 | Hoffmann | |

(56) References Cited

U.S. PATENT DOCUMENTS

| | | |
|---|---|---|
| 2008/0044481 A1 | 2/2008 | Harel |
| 2008/0045557 A1 | 2/2008 | Grainger et al. |
| 2008/0086216 A1 | 4/2008 | Wilson et al. |
| 2008/0109017 A1 | 5/2008 | Herweck et al. |
| 2008/0113001 A1 | 5/2008 | Herweck et al. |
| 2008/0118550 A1 | 5/2008 | Martakos et al. |
| 2008/0160307 A1 | 7/2008 | Bauchet |
| 2008/0206305 A1 | 8/2008 | Herweck et al. |
| 2008/0279929 A1 | 11/2008 | Devane et al. |
| 2008/0286440 A1 | 11/2008 | Scheer |
| 2008/0289300 A1 | 11/2008 | Gottlieb et al. |
| 2009/0011116 A1 | 1/2009 | Herweck et al. |
| 2009/0047414 A1 | 2/2009 | Corbeil et al. |
| 2009/0092665 A1 | 4/2009 | Mitra et al. |
| 2009/0181074 A1 | 7/2009 | Makower et al. |
| 2009/0181937 A1 | 7/2009 | Faucher et al. |
| 2009/0208552 A1 | 8/2009 | Faucher et al. |
| 2010/0183697 A1 | 7/2010 | Swanick et al. |
| 2010/0209473 A1 | 8/2010 | Dhont et al. |
| 2010/0233232 A1 | 9/2010 | Swanick et al. |
| 2011/0045050 A1 | 2/2011 | Elbayoumi et al. |
| 2011/0274823 A1 | 11/2011 | Labrecque et al. |
| 2012/0016038 A1 | 1/2012 | Faucher et al. |
| 2012/0213839 A1 | 8/2012 | Faucher et al. |

FOREIGN PATENT DOCUMENTS

| | | |
|---|---|---|
| EP | 0623354 | 11/1994 |
| EP | 0730864 | 9/1996 |
| EP | 0790822 | 8/1997 |
| EP | 0873133 | 10/1998 |
| EP | 0917561 | 5/1999 |
| EP | 1140243 | 10/2001 |
| EP | 1181943 | 2/2002 |
| EP | 1270024 | 1/2003 |
| EP | 1273314 A1 | 1/2003 |
| EP | 1364628 | 11/2003 |
| EP | 1520795 | 4/2005 |
| EP | 1557183 | 7/2005 |
| EP | 2083875 | 8/2009 |
| EP | 1402906 | 6/2011 |
| KR | 20080025986 | 3/2008 |
| WO | WO 86/00912 | 2/1986 |
| WO | WO 90/01969 | 3/1990 |
| WO | 90/08544 A1 | 8/1990 |
| WO | WO 95/26715 | 10/1995 |
| WO | WO 97/02042 | 1/1997 |
| WO | WO 97/09367 | 3/1997 |
| WO | WO 97/13528 | 4/1997 |
| WO | WO 98/30206 | 7/1998 |
| WO | 98/46287 A2 | 10/1998 |
| WO | WO 98/54275 | 12/1998 |
| WO | WO 99/25336 | 5/1999 |
| WO | WO-00/40278 A1 | 7/2000 |
| WO | WO 00/62830 | 10/2000 |
| WO | WO-00/62830 | 10/2000 |
| WO | WO 01/24866 | 4/2001 |
| WO | WO 01/26585 | 4/2001 |
| WO | WO 01/37808 | 5/2001 |
| WO | WO 01/60586 | 8/2001 |
| WO | WO 01/66036 | 9/2001 |
| WO | WO 01/76649 | 10/2001 |
| WO | WO 02/49535 | 6/2002 |
| WO | WO-02/100455 | 12/2002 |
| WO | WO 02/100455 | 12/2002 |
| WO | WO-03/000308 A1 | 1/2003 |
| WO | WO 03/015748 | 2/2003 |
| WO | WO 03/028622 | 4/2003 |
| WO | WO 03/037397 | 5/2003 |
| WO | WO 03/037398 | 5/2003 |
| WO | WO 03/039612 | 5/2003 |
| WO | WO 03/041756 | 5/2003 |
| WO | WO 03039612 A1 * | 5/2003 |
| WO | WO 03/070125 | 8/2003 |
| WO | WO 03/092741 | 11/2003 |
| WO | WO 03/092779 | 11/2003 |
| WO | WO 2004/004598 | 1/2004 |
| WO | WO 2004/006976 | 1/2004 |
| WO | WO 2004/006978 | 1/2004 |
| WO | WO 2004/028583 | 4/2004 |
| WO | WO 2004/091684 | 10/2004 |
| WO | WO 2004101010 A1 * | 11/2004 |
| WO | WO 2005/000165 | 1/2005 |
| WO | WO 2005/016400 | 2/2005 |
| WO | WO 2005/053767 | 6/2005 |
| WO | WO 2005/073091 | 8/2005 |
| WO | 2005/082434 A2 | 9/2005 |
| WO | WO 2005082434 A2 * | 9/2005 |
| WO | WO 2005/116118 | 12/2005 |
| WO | WO 2006/024488 | 3/2006 |
| WO | WO 2006/036967 | 4/2006 |
| WO | WO 2006/102374 | 9/2006 |
| WO | WO 2007/047028 | 4/2007 |
| WO | 2008/010788 A2 | 1/2008 |
| WO | 2008/016664 A2 | 2/2008 |
| WO | WO 2008/057328 | 5/2008 |
| WO | 2010/042134 A1 | 4/2010 |
| WO | 2010/042241 A1 | 4/2010 |
| WO | WO 2012/009707 | 1/2012 |

OTHER PUBLICATIONS

Polymer—Academic Press Dictionary of Science and TechnologyC. Morris (Ed.), Academic Press Dictionary of Science and Technology. Oxford, United Kingdom: Elsevier Science & Technology. Retrieved from http://search.credoreference.com/content/entry/apdst/polymer/0.*
Falagas et al. European Society of Clinical Microbiology and Infection Diseases 2005 11:3-8.*
Bimbo INFORM 1998 9(5):473-483.*
Henderson et al. Lipids 1993 28(4):313-319.*
A paper entitled, "Evaluation of the Biocompatibility and Drug Delivery Capabilities of Biological Oil Based Stent Coatings," by Li, Shengqiao of the Katholieke Universiteit Leuven.
Final Office Action for U.S. Appl. No. 11/701,799 (listed on SB/08 as US 2008-0109017), dated Feb. 13, 2012.
Ackman, R G., "Fish Oils", *Bailey's Industrial Oil and Fat Products*, 6$^{th}$ Edition, 279-317 (2005).
Ahuja et al., "Prevention of Postoperative Intraperitoneal Adhesions—An Experimental Study in Rats", *Journal of Indian Pediatric Surgery* , 7:15-20 (2002).
Andes, et al. "Antiproliferative Strategies for the Treatment of Vascular Proliferative Disease", *Current Vascular Pharmacology*, 1)1): 85-98 (2003).
Winter, et al., "Physical and Chemical Gelation" *Encyclopedia of Materials—Science and Technology*, vols. 1-11: 6691-6999 (2001).
Supplementary European Search Report for European Patent Application No. EP 12004057, dated Apr. 10, 2013.
International Search Report for International Application PCT/US05/034941, dated May 4, 2006.
International Search Report for PCT/US2011/44292, dated Dec. 6, 2011.
Notice of Allowance for U.S. Appl. No. 11/525,390 (listed on SB/08 as US-2007/0071798), dated Oct. 4, 2012.
Advisory Action for U.S. Appl. No. 12/581,582 (listed on SB-08 as U.S. Publication No. 20100183697), dated Nov. 14, 2012.
Notice of Allowance for U.S. Appl. No. 11/525,390 (listed on SB-08 as U.S. Publication No. US-2007-0071798), dated Nov. 20, 2012.
Non-Final Office Action for U.S. Appl. No. 13/404,487 (listed on SB-08 as US 20120213839), dated Dec. 20, 2012.
Non-Final Office Action for U.S. Appl. No. 13/184,512 (listed on SB-08 as 2012-0016038), dated Jan. 31, 2013.
Non-Final Office Action for U.S. Appl. No. 11/978,840 (listed on SB-08 as U.S. Publication No. US-2008-0118550), dated Feb. 19, 2013.
Non-Final Office Action for U.S. Appl. No. 13/682,991 (listed on SB-08 as U.S. Publication No. US- 2013-0074452), dated Mar. 18, 2013.
Notice of Allowance for U.S. Appl. No. 13/404,487 (listed on SB-08 as U.S. Publication No. US- 2012-0213839), dated Apr. 2, 2013.

(56) References Cited

OTHER PUBLICATIONS

Non-Final Office Action for U.S. Appl. No. 11/236,943 (listed on SB-08 as U.S. Publication No. US-2006-0067975), dated Apr. 22, 2013.
Lipids, Chapter 19, pp. 1-12 (2002).
Jorge, N., "Granas y Aceites", 48(1): 17-24, (1997).
Final Office Action for U.S. Appl. No. 13/184,512 (listed on SB-08 as U.S. Publication No. U.S. 2012-0016038), dated Jun. 25, 2013.
Non-Final Office Action for U.S. Appl. No. 11/237,264 (listed on SB-08 as U.S. Publication No. US-2006-0067983), dated Jul. 3, 2013.
Non-Final Office Action for U.S. Appl. No. 13/593,656 (listed on SB-08 as U.S. Publication No. US-2012-03115219), dated Jul. 15, 2013.
Notice of Allowance for U.S. Appl. No. 13/682,991 (listed on SB-08 as U.S. Publication No. US 2013-0074452), dated Aug. 1, 2013.
Notice of Allowance for U.S. Appl. No. 11/978,840 (listed on SB-08 as U.S. Publication No. US-2008-0118550), dated Aug. 6, 2013.
Supplementary European Search Report for Application No. EP09819594.4, dated Aug. 14, 2012.
Supplementary European Search Report for Application No. EP 08877338.7, dated Aug. 16, 2012.
Final Office Action for U.S. Appl. No. 12/182,261 (listed on SB-08 as US 2009/0047414) dated Apr. 30, 2012.
Final Office Action for U.S. Appl. No. 12/401,243 (listed on SB/08 as US-2010/0233232), dated Jun. 11, 2012.
Notice of Allowance for U.S. Appl. No. 12/182,261 (listed on SB/08 as US US-2009/0047414), dated Jul. 23, 2012.
Notice of Allowance for U.S. Appl. No. 11/236,908 (listed on SB/08 as US-2006/0067974), dated May 11, 2012.
Advisory Action for U.S. Appl. No. 12/401,243 (listed on SB/08 as US 2010-0233232), dated Aug. 27, 2012.
Final Office Action for U.S. Appl. No. 12/581,582 (listed on SB-08 as US 2010/0183697) dated Aug. 29, 2012.
Non-Final Office Action for U.S. Appl. No. 12/581,582 (listed on SB-08 as US 2010-0183697) dated Mar. 14, 2012.
Final Office Action for U.S. Appl. No. 12/185,165 (listed on SB-08 as US 2009-0011116) dated Apr. 6, 2012.
International Search Report for International Application PCT/US2013/044653, dated Sep. 4, 2013.
"Polymerization" Merriam-Webster Online Dictionary, retrieved from <www.merriam-webster.com> on Dec. 13, 2009; Merriam-Webster's Inc. 2009; pp. 1.
Autosuture, "ParietexTM Composite OS Series Mesh," retrieved online at http://www.autosuture.com/AutoSuture/pagebuilder. aspx?topicID=135734&breadcrumbs=135 601:0 (2007).
Camurus, "In our endeavors to create the unique, we start with the best. Your product."
De Scheerder, Ivan K. et al. "Biocompatibility of polymer-coated oversized metallic stents implanted in normal porcine coronary arteries," Atherosclerosis, vol. 114:105-114.
Drummond, Calum J, et al., "Surfactant self-assembly objects as novel drug delivery vehicles," Current Opinion in Colliod & Interface Science, vol. 4:449-456 (2000).
Engstrom, Sven, "Drug Delivery from Cubic and Other Lipid-water Phases," Lipid Technology, vol. 2(2):42-45 (1990).
Guler, et al. "Some empirical equations for oxopolymerization of linseed oil," Progress in Organic Coatings, vol. 51:365-371 (2004).
Hwang, Chao-Wei et al, "Physiological Transport Forces Govern Drug Distribution for Stent-Based Delivery," Circulation, vol. 104:600-605 (2001).
Jonasson, Lena et al., "Cyclosporon A inhibits smooth muscle proliferation in the vascular response to injury," Proc. Natl. Acad. Sci. USA, vol. 85: 2303-2306 (1988).
Oberhoff, Martin et al, "Local and Systemic Delivery of Low Molecular Weight Heparin Following PTCA: Acute Results and 6-Month Follow-Up of the Initial Clinical Experience With the Porous Balloon (PILOT—Study)," Catheterization and Cardiovascular Diagnosis, vol. 44:267-274 (1998).
Ogunniyi, D.S., "Castor oil: A vital industrial raw material," Biosource Technology, vol. 97: 1086-1091 (2006).
Redman, L.V. et al., "The drying rate of raw paint oils—a comparison," The Journal of Industrial and Engineering Chemistry, vol. 5: 630-636 (1913).
Rutkow, Ira M. et al., "'Tension-free' inguinal herniorrhaphy: A preliminary report on the 'mesh plug' technique," Surgery, vol. 114:3-8 (1993).
Salu, Koen J. et al, "Addition of cytochalasin D to a biocompatible oil stent coating inhibits intimal hyperplasia in a porcine coronary model," Coronary Artery Disease, vol. 14(8):545-555 (2003).
Scheller, Bruno et al, "Addition of Paclitaxel to Contrast Media Prevents Restenosis After Coronary Stent Implantation," Journal of the American College of Cardiology, vol. 42(8):1415-1420 (2003).
Shahidi, Fereidoon ed.; "Bailey's Industrial Oil and Fats Products" 2005; John Wiley and Sons; vol. 5, Edible Oil and Fat Products: Processing Technologies, pp. 1-15.
Van der Giessen, Willem J. et al, "Marked Inflammatory Sequelae to Implantation of Biodegradable and Nonbiodegradable Polymers in Porcine Coronary Arteries," Circulation, vol. 94:1690-1697 (1996).
Websters Dictionary Online, Accessed on Feb. 13, 2009, entry for "polymer" p. 1 of 1.
Binder et al., "Chromatographic Analysis of Seed Oils. Fatty Acid Composition of Castor Oil," The Journal of the American Oil Chemists' Society, vol. 39:513-517 (1962).
CECW-EE, "Ch. 4: Coating Types and Characteristics," Engineering and Design—Painting: New Construction and Maintenance, pp. 4-1 to 4-24 (1995).
Wikipedia, "Sirolimus," pp. 1-13, available online at http://en.wikipedia.org/wiki/Sirolimus, date accessed May 11, 2011.
Crivello et al., "Epoxidized triglycerides as renewable monomers in photoinitiated cationic polymerization," Chem. Mater, 1992:692-699.
Encylopedia Britannica Online, "Surface Coating," available online at http://www.britannica.com/EBchecked/topic/575029/surface-coating>, date accessed Jun. 17, 2011.
International Search Report for International Application PCT/US05/034601, dated Apr. 10, 2006.
International Search Report for International Application PCT/US05/034610, dated Mar. 16, 2006.
International Search Report for International Application PCT/US05/034614, dated Aug. 29, 2006.
International Search Report for International Application PCT/US05/034615, dated May 16, 2006.
International Search Report for International Application PCT/US05/034678, dated Aug. 28, 2006.
international Search Report for International Application PCT/US05/034681, dated Jul. 26, 2006.
International Search Report for International Application PCT/US05/034682, dated Jul. 20, 2006,.
International Search Report for International Application PCT/US05/034836, dated Jul. 6, 2006.
International Search Report for International Application PCT/US06/037184, dated Feb. 22, 2007.
International Preliminary Report on Patentability for International Application PCT/US06/040753, dated Oct. 3, 2008.
International Search Report for International Application PCT/US06/040753, dated Sep. 24, 2007.
International Search Report for International Application PCT/US07/019978, dated May 7, 2009.
International Search Report for International Application PCT/US07/022860, dated Apr. 22, 2009.
International Search Report for International Application PCT/US07/022944, dated Apr. 8, 2009.
International Search Report for International Application PCT/US08/000565, dated May 4, 2009.
International Preliminary Examination Report for International Application PCT/US08/071547, dated Aug. 26, 2010.
International Search Report for International Application PCT/US08/071547, dated Oct. 22, 2008.
International Preliminary Report on Patentability for International Application PCT/US08/071565, dated Aug. 27, 2009.

(56) References Cited

OTHER PUBLICATIONS

International Search Report for International Application PCT/US08/071565, dated Nov. 10, 2008.
International Search Report for International Application PCT/US08/085386, dated Feb. 4, 2009.
International Search Report for International Application PCT/US09/037364, dated Aug. 27, 2009.
International Search Report for International Application PCT/US10/026521, dated Jun. 23, 2010.
International Search Report for International Application PCT/US10/052899, dated Jan. 10, 2011.
Supplementary European Search Report for Application No. EP 05 80 2894, dated Jul. 27, 2011.
Supplementary European Search Report in Application No. 05 800 844, dated Aug. 19, 2011.
Supplementary European Search Report in Application No. EP 05 80 4291, dated Jul. 26, 2011.
Supplementary European Search Report in Application No. EP 05 85 8430, dated Aug. 18, 2011.
Non-final Office Action for U.S. Appl. No. 11/236,908 (listed on SB/08 as US 2006/0067974), dated Mar. 25, 2006.
Final Office Action for U.S. Appl. No. 11/236,908 (listed on SB/08 as US 2006/0067974), dated May 17, 2011.
Non-final Office Action for U.S. Appl. No. 11/236,908 (listed on SB/08 as US 2006/0067974), dated Aug. 24, 2009.
Final Office Action for U.S. Appl. No. 11/236,943 (listed on SB/08 as US 2006/0067975), dated Dec. 23, 2009.
Non-Final Office Action for U.S. Appl. No. 11/236,943 (listed on SB/08 as US 2006/0067975), dated Mar. 5, 2009.
Non-final Office Action for U.S. Appl. No. 11/236,977 (listed on SB/08 as US 2006/0088596), dated Aug. 3, 2009.
Final Office Action for U.S. Appl. No. 11/237,263 (listed on SB/08 as US 2006/0110457), dated Jul. 7, 2010.
Non-final Office Action for U.S. Appl. No. 11/237,263 (listed on SB/08 as US 2006/0110457), dated Oct. 7, 2009.
Final Office Action for U.S. Appl. No. 11/237,264 (listed on SB/08 as US 2006/0067983), dated Jun. 2, 2010.
Non-final Office Action for U.S. Appl. No. 11/237,264 (listed on SB/08 as US 2006/0067983), dated Oct. 5, 2009.
Final Office Action for U.S. Appl. No. 11/701,799 (listed on SB/08 as US 2008/0109017), dated Nov. 23, 2010.
Non-final Office Action for U.S. Appl. No. 11/238,532 (listed on SB/08 as US 2006/0067976), dated Mar. 30, 2009.
Final Office Action for U.S. Appl. No. 11/238,532 (listed on SB/08 as US 2006/0067976), dated Sep. 9, 2009.
Final Office Action for U.S. Appl. No. 11/238,554 (listed on SB/08 as US 2006/0121081), dated May 12, 2010.
Non-final Office Action for U.S. Appl. No. 11/238,554 (listed on SB/08 as US 2006/0121081), dated Oct. 9, 2009.
Final Office Action for U.S. Appl. No. 11/238,554 (listed on SB/08 as US 2006/0121081), dated May 1, 2009.
Non-final Office Action for U.S. Appl. No. 11/238,554 (listed on SB/08 as US 2006/0121081), dated Jul. 25, 2008.
Non-final Office Action for U.S. Appl. No. 11/238,564 (listed on SB/08 as US 2006/0083768), dated Apr. 16, 2008.
Final Office Action for U.S. Appl. No. 11/238,564 (listed on SB/08 as US 2006/0083768), dated Aug. 6, 2009.
Non-final Office Action for U.S. Appl. No. 11/239,555 (listed on SB/08 as US 2006/0067977), dated Mar. 30, 2009.
Non-final Office Action for U.S. Appl. No. 11/525,328 (listed on SB/08 as US 2007/0084144), dated Apr. 30, 2007.
Non-final Office Action for U.S. Appl. No. 11/525,390 (listed on SB/08 as US 2007/0071798), dated Jul. 14, 2010.
Final Office Action for U.S. Appl. No. 11/525,390 (listed on SB/08 as US 2007/0071798), dated Feb. 21, 2011.
Final Office Action for U.S. Appl. No. 11/582,135 (listed on SB/08 as US 2007/0202149), dated May 12, 2011.
Non-final Office Action for U.S. Appl. No. 11/582,135 (listed on SB/08 as US 2007/0202149), dated Nov. 9, 2010.
Non-final Office Action for U.S. Appl. No. 11/582,135 (listed on SB/08 as US 2007/0202149), dated Jan. 6, 2010.
Non-final Office Action for U.S. Appl. No. 11/582,135 (listed on SB/08 as US 2007/0202149), dated May 12, 2009.
Non-final Office Action for U.S. Appl. No. 11/701,799 (listed on SB/08 as US 2008/0109017), dated Apr. 12, 2010.
Non-final Office Action for U.S. Appl. No. 11/978,840 (listed on SB/08 as US 2008/0118550), dated Dec. 3, 2010.
Non-final Office Action for U.S. Appl. No. 11/980,155 (listed on SB/08 as US 2008/0113001), dated Mar. 24, 2011.
Non-final Office Action for U.S. Appl. No. 12/075,223 (listed on SB/08 as US 2008/0206305), dated Dec. 8, 2010.
Non-final Office Action for U.S. Appl. No. 12/325,546 (listed on SB/08 as US 2009/0181937), dated Feb. 25, 2010.
Final Office Action for U.S. Appl. No. 12/325,546 (listed on SB/08 as US 2009/0181937), dated Aug. 31, 2010.
Non-final Office Action for U.S. Appl. No. 12/364,763 (listed on SB/08 as US 2009/0208552), dated Dec. 11, 2009.
Final Office Action for U.S. Appl. No. 12/364,763 (listed on SB/08 as US 2009/0208552), dated Sep. 21, 2010.
Interview summary for U.S. Appl. No. 11/236,908 (listed on SB/08 as US 2006/0067974) dated May 5, 2009.
Interview summary for U.S. Appl. No. 11/236,908 (listed on SB/08 as US 2006/0067974) dated Dec. 2, 2010.
Interview summary for U.S. Appl. No. 11/582,135 (listed on SB/08 as US 2007/0202149) dated Dec. 7, 2010.
Interview summary for U.S. Appl. No. 12/325,546 (listed on SB/08 as US 2009/0181937) dated Dec. 2, 2010.
Interview summary for U.S. Appl. No. 12/364,763 (listed on SB/08 as US 2009/0208552) dated Dec. 2, 2010.
Final Office Action for U.S. Appl. No. 11/978,840 (listed on SB/08 as US 2008/0118550), dated Jun. 22, 2011.
Non-final Office Action for U.S. Appl. No. 11/525,390 (listed on SB/08 as US 2007/0071798), dated Jul. 11, 2011.
Non-Final Office Action for U.S. Appl. No. 11/701,799 (listed on SB/08 as US 2008/0109017), dated Aug. 17, 2011.
Final Office Action for U.S. Appl. No. 11/980,155 (listed on SB/08 as US 2008/0113001), dated Oct. 21, 2011.
Non-Final Office Action for U.S Appl. No. 12/182,261 (listed on SB/08 as US 2009/0047414), dated Dec. 21, 2011.
Non-Final Office Action for U.S. Appl. No. 11/236,908 (listed on SB/08 as US 2006/0067974), dated Dec. 2, 2011.
Non-Final Office Action for U.S. Appl. No. 11/582,135 (listed on SB/08 as US 2007/0202149), dated Oct. 14, 2011.
Non-Final Office Action for U.S. Appl. No. 12/182,165 (listed on SB/08 as US 2009/0011116), dated Jan. 5, 2012.
Non-Final Office Action for U.S. Appl. No. 12/401,243 (listed on SB/08) as US 2010/0233232, dated Jan. 5, 2012.
Notice of Allowance for U.S. Appl. No. 11/582,135 (listed on SB/08 as US 2007/0202149), dated Jan. 9, 2012.
Final Office Action for U.S. Appl. No. 12/075,223 (listed on SB/08 as US 2008/0206305), dated Aug. 11, 2011.
Non-Final Office Action for U.S. Appl. No. 12/075,223 (listed on SB-08 as U.S. Publication No. US-2008-0206305), dated Nov. 12, 2013.
Non-Final Office Action for U.S. Appl. No. 11/980,155 (listed on SB-08 as U.S. Publication No. US-2008-0113001), dated Nov. 12, 2013.
Final Office Action for U.S. Appl. No. 11/236,943 (listed on SB-08 as U.S. Publication No. US- 2006-0067975), dated Dec. 4, 2013.
Final Office Action for U.S. Appl. No. 11/237,264 (listed on SB-08 as U.S. Publication No. US-2006-0067983), dated Dec. 17, 2013.
Notice of Allowance for U.S. Appl. No. 13/593,656 (listed on SB-08 as U.S. Publication 2012-03115219), dated Jan. 24, 2014.
Notice of Allowance for U.S. Appl. No. 11/237,263 (listed on SB-08 as U.S. Publication No. US-2006-0110457), dated Mar. 27, 2014.
Non Final Office Action for U.S. Appl. No. 12/325,546 (listed on SB-08 as U.S. Publication No. US-2009-0181937), dated Apr. 22, 2014.
Non Final Office Action for U.S. Appl. No. 12/364,763 (listed on SB-08 as U.S. Publication No. US-2009-0208552), dated Apr. 23, 2014.

(56) References Cited

OTHER PUBLICATIONS

Non-Final Office Action for U.S. Appl. No. 12/401,243 (listed on SB/08 as US 2010-0233232), dated May 8, 2014.
Supplementary European Search Report for Application No. EP 10825447, dated Mar. 31, 2014.
Uchida, et al., "Swelling Process and Order-Disorder Transition of Hydrogel Containing Hydrophobic Ionizable Groups", *Macromolecules*, 28, 4583-4586 (1995).
Gutfinger, et al., "Polyphenols in Olive Oils", *Journal of the American Oil Chemists Society*, 58(11): 966-968 (1981).
Portilla, et al., "Prevention of Peritoneal Adhesions by Intraperitoneal Administration of Vitamin E: An Experimental Study in Rats", *Diseases of the Colon and Rectum*, 47; 2157-2161 (2005).
Sano, et al., "A controlled Trial of Selegiline, Alpha-Tocopherol, or Both as Treatment for Alzheimer's Disease", *The New England Journal of Medicine*, 336; 1216-1222 (1997).
Non-Final Office Action for U.S. Appl. No. 13/943,489, dated Jul. 1, 2014.
Final Office Action for U.S. Appl. No. 11/980,155, dated Jul. 21, 2014.
Non-Final Office Action for U.S. Appl. No. 11/701,799, dated Jul. 22, 2014.
Final Office Action for U.S. Appl. No. 12/075,223, dated Jul. 22, 2014.
Non-Final Office Action for U.S. Appl. No. 13/843,068, dated Sep. 29, 2014.
Notice of Allowance for U.S. Appl. No. 11/236,943 (listed on SB-08 as U.S. Publication No. US-2006-0067975), dated Oct. 6, 2014.
Non-Final Office Action for U.S. Appl. No. 13/184,512, dated Oct. 10, 2014.
Non-Final Office Action for U.S. Appl. No. 12/075,223, dated Oct. 29, 2014.
Non-Final Office Action for U.S. Appl. No. 11/980,155, dated Nov. 7, 2014.
Notice of Allowance for U.S. Appl. No. 12/364,763 (listed on SB-08 as U.S. Publication No. US-2009-0208552), dated Dec. 5, 2014.
Notice of Allowance for U.S. Appl. No. 12/325,546 (listed on SB-08 as U.S. Publication No. US-2009-0181937), dated Dec. 8, 2014.
Final Office Action for U.S. Appl. No. 12/581,582, dated Jan. 8, 2015.
Final Office Action for U.S. Appl. No. 12/401,243, dated Jan. 16, 2015.
Notice of Allowance for U.S. Appl. No. 13/943,489, dated Jan. 29, 2015.
Final Office Action for U.S. Appl. No. 11/701,799, dated Mar. 12, 2015.
Final Office Action for U.S. Appl. No. 13/843,068, dated Apr. 23, 2015.
Final Office Action for U.S. Appl. No. 13/184,512, dated Apr. 28, 2015.
Hortolam, Juliane G., et al., "Connective tissue diseases following silicone breast implantation: where do we stand?", Clinics, 2013, vol. 3, p. 281.
Lidar, M., et al., "Silicone and scleroderma revisited", Lupus, 2012, vol. 21, pp. 121-127.
"Lead", Article by Centers for Disease Control and Prevention (CDC), Nov. 2009, 2 pages.
Fineberg, H. and Johanson, A.G., Industrial Use of Fish Oils, http://spo.nmfs.noaa.gov/Circulars/CIRC278.pdf (downloaded Aug. 3, 2015).
Lewis, Richard J., Sr., Hawley's Condensed Chemical Dictionary, 2001, 308, 309 and 896-898, Fourteenth Edition, John Wiley & Sons, Inc., New York.
Oxford Reference, A Dictionary of Chemistry, 6th edition, John Daintith, 2008, 3 pages.
Fats & Oils (2008) at http://scifun.chem.wisc.edu/chemweek/pdf/fats&oils.pdf (downloaded Sep. 24, 2015).
Fish Oil Triglycerides vs. Ethyl Esters: A Comparative Review of Absorption, Stability and Safety Concerns (Ascenta Health Ltd. 2010 at http://www.ascentaprofessional.com/science/articles/fish-oil-triglycerides-vs-ethyl-esters (downloaded Sep. 24, 2015).
Webster's II New College Dictionary (1995), 1075, Houghton Mifflin Company, New York, US.
Polymers made from multiple monomers, A Natural Approach to Chemistry, Chapter 8, 241, http://lab-aids.com/assets/uploads/NAC/NAC_student_book/Texas%20Student%20Edition%20253.pdf (downloaded Dec. 3, 2015).
Polymer, Encyclopedia Britannica. Encyclopedia Britannica Online, Encyclopedia Britannica Inc., 105, Web. Dec. 2, 2015, http://www.britannica.com/print/article/468696 (downloaded Dec. 2, 2015).
SepraFilm Adhesion Barrier package insert (Genzyme Biosurgery 2008).
Sannino, Alessandro, et al., Biodegradeable Cellulose-based Hydrogels: Design and Applications, 2 Materials, pp. 353-373, 2009.
Heinz, Thomas, Carboxymethyl Ethers of Cellulose and Starch—A Review, Center of Excellence for Polysaccharide Research, Friedrich Schiller University of Jena (Germany), pp. 13-29, 2005.
Omidian, H. et al., Swelling Agents and Devices in Oral Drug Delivery, J. Drug. Del. Sci. Tech., No. 18, vol. 2, 2008, pp. 83-93.
Kamel, S. et al., Pharmaceutical Significance of Cellulose: A Review, Express Polymer Letters vol. 2, No. 11, 2008, pp. 758-778.
Adel, A. M. et al., Carboxymethylated Cellulose Hydrogel: Sorption Behavior and Characterization, Nature and Science, No. 8, vol. 8, 2010, pp. 244-256.
Bacteria in Water, The USGS Water Science School, http://water.usgs.gov/edu/bacteria.html (downloaded Nov. 9, 2015).
Novotny, L. et al., Fish: a potential source of bacterial pathogens for human beings, Vet. Med.—Czech, 49, 2004, vol. 9, pp. 343-358.
Allergies, Asthma and Allergy Foundation of America (2011), http://www.aafa.org/page/types-of-allergies,aspx (downloaded Oct. 5, 2015).
Sicherer, Scott H., Food Allergies: A Complete Guide for Eating When Your Life Depends on it, 2013, 15, Johns Hopkins University Press, Baltimore, MD, USA.
Omega-3 DHA—The Problem May Be the Quality of Your Fish Oil, Not Your Allergy to Fish, Fatty Acids Hub, http://www.fattyacidshub.com/fatty-acids/omega-3-dha/ (downloaded Nov. 10, 2015).
Soy Allergy, Asthma and Allergy Foundation of America (2005), http://www.aafa.org/display.cfm?id=9&sub=20&cont=522 (downloaded Nov. 10, 2015).
Refined soybean oil not an allergen, say food scientists, FOOD navigator-usa.com (2005), http://www.foodnavigator-usa.com/content/view/print/127438 (downloaded Nov. 10, 2015).
Yahyaee, R. et al., Waste fish oil biodiesel as a source of renewable fuel in Iran, Renewable and Sustainable Energy Reviews, 2013, pp. 312-319, 17, Elsevier Ltd.
Biological evaluation of medical devices—Part 1: Evaluation and testing, International Standard ISO 109931-1, Aug. 1, 2003, Third Edition, Switzerland.
Mayo Clinic (http://www.mayoclinic.org/drugs-supplements/omega-3-fatty-acids-fish-oil-alpha-linolenic-acids/safety/hrb-20059372?p=1 (downloaded Sep. 28, 2015).
Milk allergy, at http://www.mayoclinic.org/diseases-conditions/milk-allergy/basics/definition/con-20032147?p=1 (downloaded Jul. 29, 2015).
Soy allergy, at http://www.mayoclinicorg/diseases-conditions/soy-allergy/basics/definition/con-20031370?p=1 (downloaded Jul. 29, 2015).
F.D. Gunstone, Fatty Acid and Lipid Chemistry 72 (1999).
Hawley's Condensed Chemical Dictionary 315, 316, 332, 333, 334, 825 and 826 (2001).
Hutlin, Herbert O. et al., Chemical Composition and Stability of Fish Oil (International Association of Fish Meal Manufacturers Apr. 10, 1991).
F.V.K. Young, The Chemical & Physical Properties of Crude Fish Oils for Refiners and Hydrogenators, 18 Fish Oil Bulletin 1-18 (1986).
Karrick, Neva L., Nutritional Value of Fish Oils as Animal Feed, Circular 281 (Fish and Wildlife Service Bureau of Commercial

(56) References Cited

OTHER PUBLICATIONS

Fisheries 1967), reprinted from M.E. Stansby (ed.), Fish Oils 362-382 (Avi Publishing Company 1967).
Luley et al., Fatty acid composition and degree of peroxidation in fish oil and cod liver oil preparations, Arzneimittelforschung. Dec. 1998, vol. 38, No. 12, pp. 1783-1786.
Drying Oil, http://en.wikipedia.org/wiki/drying_oil (downloaded Jun. 28, 2013).
Szebeni et al., "Complement Activation by Cremophor EL as a Possible Contributor to Hypersensitivity to Paclitaxel: an In Vitro Study", Journal of the National Cancer Institute, 1998, vol. 90, No. 4, pp. 300-306.
Birsan, et al., "The novel calcineurin inhibitor ISA247: a more potent immunosuppressant than cyclosporine in vitro", Transpl. Int., 2005, vol. 17, pp. 767-771.
About.com, "Orthopedics, Synvisc injections," retrieved online at http://orthopedics.about.com/cs/treatment/a/synvisc_2.htm (2005).
Cath Lab Digest, "Olive Oil Emulsion Helps With Problem Heart Arteries", retrieved online at http://www.cathlabdigest.com/displaynews.cfm?newsid=0103073 (2007).
Doctor's Guide to Medical and Other News, "AAOS Meeting: Synvisc Delays Total Knee Replacement in Osteoarthritis Patients", retrieved online at http://www.docguide.com/dg.nsf/PrintPrint/4585EC355198EEF08525670E006B10FF (1999).
Methodist, "Evaluation of Biocompatibility and Antirestenotic Potential of Drug Eluting Stents Employing Polymer-free Highly-Hydrogenated Lipid-Based Stent Coatings in Porcine Coronary Arteries", Transcatheter Cardiovascular Therapeutics (TCT), sponsored by the Cardiovascular Research Foundation®, Oct. 22-27, 2006, Washington Convention Center, Washington, D.C.
Novavax, retrieved online at http://www.novavax.com/go.cfm?do=Page.View&pid=3 (2006).
Orthovisc, "New Treatment Option is Potential Alternative to OTC Pain Medications for Osteoarthritis of the Knee" retrieved online at http://www.jnj.com/innovations/new_features/ORTHOVISC.htm:jessionid=33N2RBQDVODZKCQPCCEGU3AKB2IIWTT1 (2006).
Orthovisc, "What is ORTHOVISC®?" retrieved online at http://www.orthovisc.com/xhtmlbgdisplay.jhtml?itemname=about_orthovisc (2005).
Orthovisc, "Your Knees and Osteoarthritis", retrieved online at http://www.orthovisc.com/xhtmlbgdisplay.jhtml?itemname=understanding_knee_oa (2003).
Orthovisc, "What to expect from your treatment," retrieved online at http://www.orthovisc.com/xhtmlbgdisplay.jhtml?itemname=what_to_expect (2007).
Orthovisc, "Tools and Resources for Managing Your Osteoarthritis", retrieved online at http://www.orthovisc.com/xhtmlbgdisplay.jhtml?itemname=patient_resources (2007).
Pohibinska, A., et al., "Time to reconsider saline as the ideal rinsing solution during abdominal surgery", The American Journal of Surgery, vol. 192, pp. 281-222 (2007).
Singh, Alok, et al., "Facilitated Stent Delivery Using Applied Topical Lubrication", Catherization and Cardiovascular Interventions, vol. 69, pp. 218-222 (2007).
Urakaze, Masaharu et al., "Infusion of fish oil emulsion: effects on platelet aggregation and fatty acid composition in phospholipids of plasma, platelets and red blood cell membranes in rabbits", Am. J. Clin. Nutr., vol. 46, pp. 936-940 (!987).
Triglycerides, https://www.lipid.org/sites/default/files/triglycerides.pdf (downloaded Sep. 24, 2015).
Swanson, Danielle, et al., Omega-3 Fatty Acids EPA and DHA: Health Benefits Throughout Life, 3 Advances in Nutrition 1-7 (American Society for Nutrition 2012).
Babaev, Vladimir R., et al., Macrophage Lipoprotein Lipase Promotes Foam Cell Formation and Atherosclerosis in Vivo, 103 The Journal of Clinical Investigation 1697-1705 (1999).

* cited by examiner

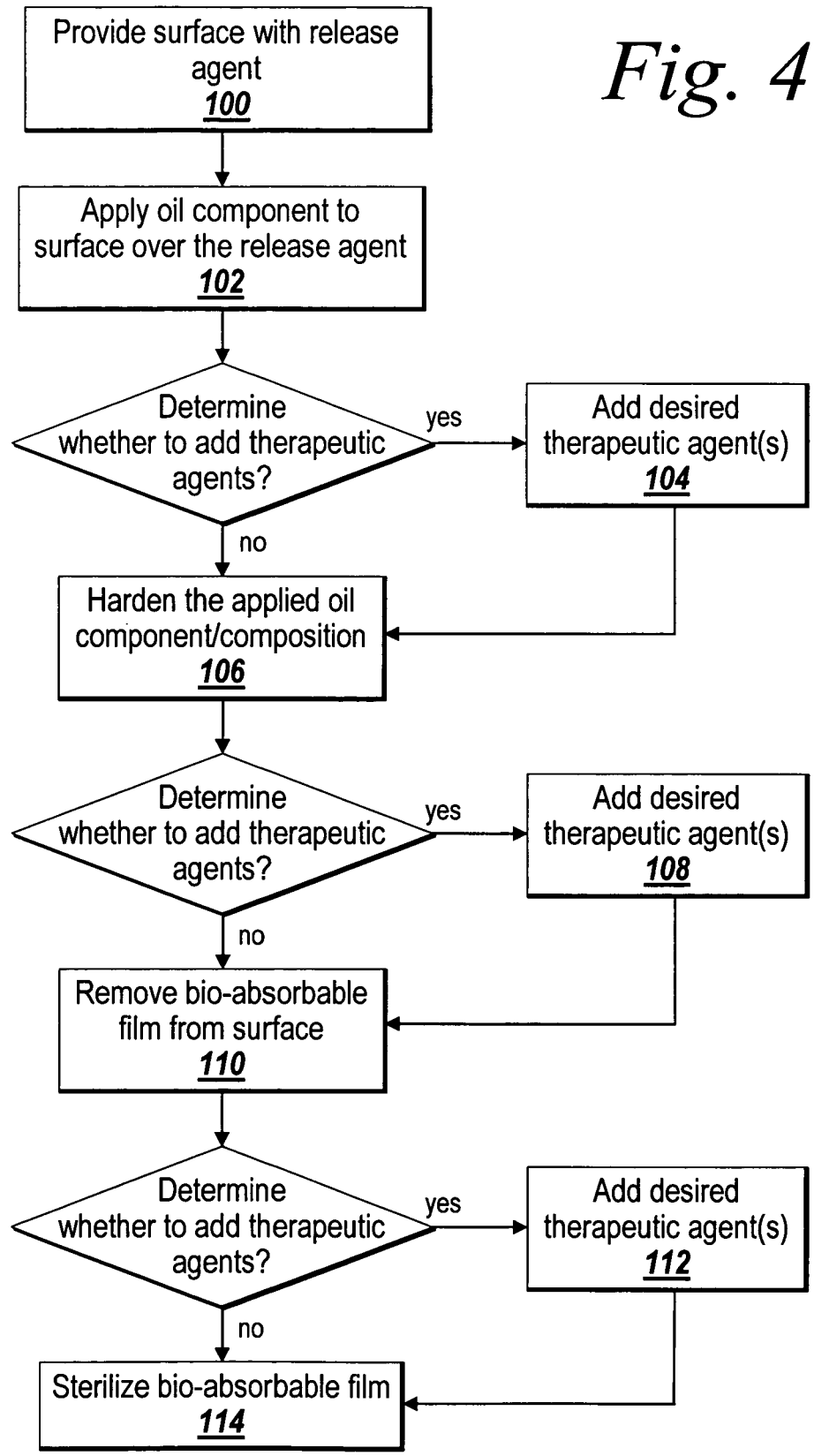

BARRIER LAYER

RELATED APPLICATIONS

This application claims priority to, and the benefit of, U.S. Provisional Application No. 60/613,808, filed Sep. 28, 2004, for all subject matter common to both applications. The disclosure of said provisional application is hereby incorporated by reference in its entirety.

FIELD OF THE INVENTION

The present invention relates to barrier layers, and more particularly to a barrier layer that is able to deliver therapeutic agents to a targeted location and also to adhere to a medical device.

BACKGROUND OF THE INVENTION

Biocompatible medical film is often used in surgical settings. For example, Seprafilm®, a product of Genzyme Corporation of Cambridge, Mass., is used in patients undergoing abdominal or pelvic laparotomy as an adjunct intended to reduce the incidence, extent, and severity of postoperative adhesions between different tissues and organs and implantable medical devices such as soft tissue support membranes and mesh.

U.S. Pat. No. 5,017,229 is directed to a water insoluble, biocompatible gel that includes the reaction product of hyaluronic acid, a polyanionic polysaccharide, and an activating agent. The gel described in the '229 patent can be provided in the form of an adhesion prevention composition, such as a membrane or composition suitable for incorporation into a syringe. The gel is described as being able to form a film by being compressed or allowed to dehydrate. When modified with polysaccharide, the film forms the above-described Seprafilm® anti-adhesion or adhesion barrier product.

However, such commercially available adhesion prevention and adhesion barrier products often are difficult to handle and apply to the targeted location due to their chemical make up and bio-dissolvable properties. The composition and structural properties of these bio-dissolvable products require that they be handled with dry hands or instruments, which can be difficult during most surgical intervention operations. Furthermore, many of these bio-dissolvable films are made intentionally to be thin to minimize tissue disruption and consequently end up being structurally weak (i.e., easily torn or folded during handling).

Surgical meshes also can have anti-adhesion properties. PCT Application Publication No. WO 2004/028583 is directed to compositions, devices, and methods for maintaining or improving the integrity of body passageways following surgery or injury. The delivery devices can include one or more therapeutic agents provided with a mesh wrap. The mesh is most often constructed of a synthetic polymer material, such as polyethylene, polytetrafluoroethylene, and polypropylene, and can include a carrier having a therapeutic agent attached thereto or coated thereon. The mesh structure makes it easier to handle the device without the drawbacks of film, namely tearing and folding.

Some of these film and mesh devices also include therapeutic agents in combination with the anti-adhesion properties. PCT Application Publication No. WO 03/028622 is directed to a method of delivering drugs to a tissue using drug coated medical devices. The drug coated medical device is brought into contact with the target tissue or circulation and the drugs are quickly released onto the area surrounding the device in a short period of time after contact is made. The release of the drug may occur over a period of 30 seconds, 1 minute or 3 minutes. In one embodiment described in the publication, the carrier of the drug is a liposome. Other particles described as potential drug carriers include lipids, sugars, carbohydrates, proteins, and the like. The publication describes these carriers as having properties appropriate for a quick short term release of a drug combined with the carriers.

SUMMARY OF THE INVENTION

What is desired is a non-polymeric biological oil based barrier layer which exhibits anti-adhesion properties without chronic inflammation to the local tissue that can also be further enhanced with the application of one or more therapeutic agents or medications for absorption into the tissue that is in contact with the biological oil layer or coating. The barrier layer can also be coated, mounted or adhered to a medical device. The present invention is directed toward further solutions to address this need.

In accordance with one embodiment of the present invention, a barrier layer device includes a medical device structure and a barrier layer formed on at least a portion of the medical device structure. The barrier layer is formed of a non-polymeric cross-linked gel.

It should be noted that the term cross-linked gel, as utilized herein with reference to the present invention, refers to a gel that is non-polymeric and is derived from an oil composition comprising molecules covalently cross-linked into a three-dimensional network by one or more of ester, ether, peroxide, and carbon-carbon bonds in a substantially random configuration. In various preferred embodiments, the oil composition comprises a fatty acid molecule, a glyceride, and combinations thereof.

In accordance with aspects of the present invention, the medical device is in the form of a biocompatible mesh. The cross-linked gel is derived from at least one fatty acid compound. The barrier layer can be a biological oil barrier, a physical anti-adhesion barrier, or a combination thereof.

In accordance with further aspects of the present invention, the cross-linked gel is formed of an oil or oil composition that is at least partially cured. The cross-linked gel can be a biological oil that is at least partially cured, including fish oil or other oils, including those oils containing lipids and/or omega-3 fatty acids.

Curing with respect to the present invention generally refers to thickening, hardening, or drying of a material brought about by heat, UV light, chemical means, and/or reactive gasses.

In accordance with further aspects of the present invention, the barrier layer includes at least one therapeutic agent component. The therapeutic agent component can include an agent selected from the group consisting of antioxidants, anti-inflammatory agents, anti-coagulant agents, drugs to alter lipid metabolism, anti-proliferatives, anti-neoplastics, tissue growth stimulants, functional protein/factor delivery agents, anti-infective agents, imaging agents, anesthetic agents, chemotherapeutic agents, tissue absorption enhancers, anti-adhesion agents, germicides, analgesics, prodrugs, and antiseptics.

In accordance with further aspects of the present invention, the barrier layer includes a plurality of tiers. A first tier can be configured on the medical device structure and a second tier configured on the first tier, wherein the first tier is cured to a greater extent than the second tier. Alternatively, a first tier can be configured on the medical device structure and a second tier configured on the first tier, wherein the second tier is cured to a greater extent than the first tier.

In accordance with further aspects of the present invention, the barrier layer is configured to provide controlled release of a therapeutic agent component.

In accordance with further aspects of the present invention, the barrier layer includes an oil composition that includes an oil component in combination with at least one of an additional oil component, a therapeutic agent component, a solvent, and a preservative. The barrier layer is bio-absorbable. The biological oil barrier layer maintains anti-inflammatory and/or non-inflammatory properties.

In accordance with aspects of the present invention, the barrier layer is formed of a cured cross-linked gel derived from at least one fatty acid compound and containing an interdispersed biological oil, such that the cured cross-linked gel and the biological oil create a biological oil barrier and a physical anti-adhesion barrier on the medical device.

The barrier layer can be configured on one side of the medical device structure, on a portion of one side of the medical device structure, and/or on two sides of the medical device structure.

The barrier layer can further include alpha tocopherol or a derivative or analog thereof to at least partially form the barrier layer.

In accordance with one embodiment of the present invention, a barrier layer device includes a biocompatible mesh structure, and a barrier layer formed on at least a portion of the mesh structure. The barrier layer is formed of a non-polymeric cross-linked gel providing a biological oil barrier and a physical anti-adhesion barrier.

In accordance with one embodiment of the present invention, a method of making a barrier layer device includes providing a medical device structure, and creating a barrier layer formed on at least a portion of the medical device structure. The barrier layer is formed of a non-polymeric cross-linked gel.

In accordance with aspects of the present invention, creating the barrier layer includes providing a biological oil or oil composition, applying the oil or oil composition to the medical device structure, and curing the oil or oil composition on the medical device structure to form the barrier layer. In accordance with further aspects of the present invention, the method further includes partially curing the biological oil or oil composition prior to applying the oil or oil composition to the medical device structure to thicken the oil or oil composition.

In accordance with further aspects of the present invention, the method further includes applying the oil or oil composition using multiple tiers. An additional tier of oil or oil composition can likewise be applied after curing the oil or oil composition on the medical device.

In accordance with further aspects of the present invention, the step of curing includes applying a curing mechanism, such as heat, UV light, chemical means, or reactive gases.

BRIEF DESCRIPTION OF THE DRAWINGS

The aforementioned features and advantages, and other features and aspects of the present invention, will become better understood with regard to the following description and accompanying drawings, wherein:

FIG. 4 is a flow chart illustrating a method of making the barrier layer of the present invention, in accordance with one embodiment of the present invention;

DETAILED DESCRIPTION

Figure 1:
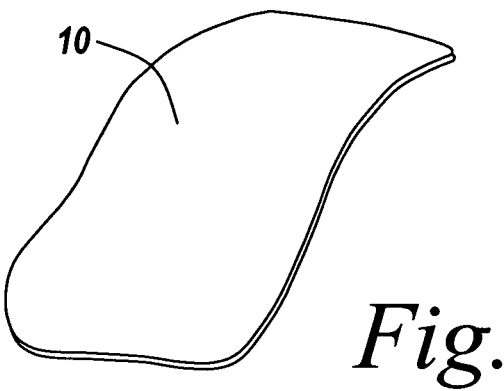
FIG. 1 is a diagrammatic illustration of a barrier layer realized as a stand alone film, according to one embodiment of the present invention.

An illustrative embodiment of the present invention relates to the provision of a barrier layer that can exhibit anti-inflammatory properties, non-inflammatory properties, and anti-adhesion properties, and corresponding method of making. The barrier layer can be its own medical device (i.e., a stand alone film), or the barrier layer can be combined with another medical device to provide anti-adhesion characteristics, in addition to improved healing and delivery of therapeutic agents. The barrier layer is generally formed of a naturally occurring oil, or an oil composition formed in part of a naturally occurring oil. In addition, the oil composition can include a therapeutic agent component, such as a drug or other bioactive agent. The barrier layer is implantable in a patient for short term or long term applications, and can include controlled release of the therapeutic agent. As implemented herein, the barrier layer is a non-polymeric cross-linked gel derived at least in part from a fatty acid compound.

As utilized herein, the term "bio-absorbable" generally refers to having the property or characteristic of being able to penetrate the tissue of a patient's body. In certain embodiments of the present invention bio-absorption occurs through a lipophilic mechanism. The bio-absorbable substance is soluble in the phospholipid bi-layer of cells of body tissue, and therefore impacts how the bio-absorbable substance penetrates into the cells.

It should be noted that a bio-absorbable substance is different from a biodegradable substance. Biodegradable is generally defined as capable of being decomposed by biological agents, or capable of being broken down by microorganisms or biological processes, in a manner that does not result in cellular uptake of the biodegradable substance. Biodegradation thus relates to the breaking down and distributing of a substance through the patient's body, verses the penetration of the cells of the patient's body tissue. Biodegradable substances, such as polymers, can cause inflammatory response due to either the parent substance or those substances formed during breakdown, and they may or may not be absorbed by tissues. Bio-absorbable substances break down into substances or components that do not cause an inflammatory response and can be consumed by the cells forming the body tissues.

The phrase "controlled release" generally refers to the release of a biologically active agent in a predictable manner over the time period of weeks or months, as desired and predetermined upon formation of the biologically active agent on the medical device from which it is being released. Controlled release includes the provision of an initial burst of release upon implantation, followed by the predictable release over the aforementioned time period.

With regard to the aforementioned oils, it is generally known that the greater the degree of unsaturation in the fatty acids the lower the melting point of a fat, and the longer the hydrocarbon chain the higher the melting point of the fat. A polyunsaturated fat, thus, has a lower melting point, and a saturated fat has a higher melting point. Those fats having a lower melting point are more often oils at room temperature. Those fats having a higher melting point are more often waxes or solids at room temperature. Therefore, a fat having the physical state of a liquid at room temperature is an oil. In general, polyunsaturated fats are liquid oils at room temperature, and saturated fats are waxes or solids at room temperature.

Polyunsaturated fats are one of four basic types of fat derived by the body from food. The other fats include saturated fat, as well as monounsaturated fat and cholesterol. Polyunsaturated fats can be further composed of omega-3 fatty acids and omega-6 fatty acids. Under the convention of naming the unsaturated fatty acid according to the position of its first double bond of carbons, those fatty acids having their first double bond at the third carbon atom from the methyl end of the molecule are referred to as omega-3 fatty acids. Likewise, a first double bond at the sixth carbon atom is called an omega-6 fatty acid. There can be both monounsaturated and polyunsaturated omega fatty acids.

Omega-3 and omega-6 fatty acids are also known as essential fatty acids because they are important for maintaining good health, despite the fact that the human body cannot make them on its own. As such, omega-3 and omega-6 fatty acids must be obtained from external sources, such as food. Omega-3 fatty acids can be further characterized as containing eicosapentaenoic acid (EPA), docosahexanoic acid (DHA), and alpha-linolenic acid (ALA). Both EPA and DHA are known to have anti-inflammatory effects and wound healing effects within the human body.

Oil that is hydrogenated becomes a waxy solid. Attempts have been made to convert the polyunsaturated oils into a wax or solid to allow the oil to adhere to a device for a longer period of time. One such approach is known as hydrogenation, which is a chemical reaction that adds hydrogen atoms to an unsaturated fat (oil) thus saturating it and making it solid at room temperature. This reaction requires a catalyst, such as a heavy metal, and high pressure. The resultant material forms a non-crosslinked semi-solid. Hydrogenation can reduce or eliminate omega-3 fatty acids, and any therapeutic effects (both anti-inflammatory and wound healing) they offer.

For long term controlled release applications, polymers, as previously mentioned, have been utilized in combination with a therapeutic agent. Such a combination provides a platform for the controlled long term release of the therapeutic agent from a medical device. However, polymers have been determined to themselves cause inflammation in body tissue. Therefore, the polymers often must include at least one therapeutic agent that has an anti-inflammatory effect to counter the inflammation caused by the polymer delivery agent. In addition, patients that receive a polymer-based implant must also follow a course of systemic anti-inflammatory therapy, to offset the inflammatory properties of the non-absorbable polymer. Typical anti-inflammatory agents are immunosupressants and systemic delivery of anti-inflammatory agents can sometimes lead to additional medical complications, such as infection or sepsis, which can lead to long term hospitalization or death. Use of the non-polymeric cross-linked gel of the inventive coating described herein can negate the necessity of anti-inflammatory therapy, and the corresponding related risks described, because there is no inflammatory reaction to the oil barrier.

In addition, some curing methods have been indicated to have detrimental effects on the therapeutic agent combined with the omega-3 fatty acid, making them partially or completely ineffective. As such, oils, and more specifically oils containing omega-3 fatty acids, have been utilized as a delivery agent for the short term uncontrolled release of a therapeutic agent, so that minimal or no curing is required. However, there are no known uses of oils containing omega-3 fatty acids for combination with a therapeutic agent in a controlled release application that makes use of the therapeutic benefits of the omega-3 fatty acids. Further, some heating of the omega-3 fatty acids to cure the oil can lessen the total therapeutic effectiveness of the omega-3 fatty acids, but not eliminate the therapeutic effectiveness. One characteristic that can remain after certain curing by heating methods is the non-inflammatory response of the tissue when exposed to the cured omega-3 fatty acid material. As such, an oil containing omega-3 fatty acids can be heated for curing purposes, and still maintain some or even a majority of the therapeutic effectiveness of the omega-3 fatty acids. In addition, although the therapeutic agent combined with the omega-3 fatty acid and cured with the omega-3 fatty acid can be rendered partially ineffective, the portion remaining of the therapeutic agent can, in accordance with the present invention, maintain pharmacological activity and in some cases be more effective than an equivalent quantity of agent delivered with other barrier or coating materials.

It should be noted that as utilized herein to describe the present invention, the term vitamin E and the term alpha-tocopherol, are intended to refer to the same or substantially similar substance, such that they are interchangeable and the use of one includes an implicit reference to both. Further included in association with the term vitamin E are such variations including but not limited to one or more of alpha-tocopherol, beta-tocopherol, delta-tocopherol, gamma-tocopherol, alpha-tocotrienol, beta-tocotrienol, delta-tocotrienol, gamma-tocotrienol, alpha-tocopherol acetate, beta-tocopherol acetate, gamma-tocopherol acetate, delta-tocopherol acetate, alpha-tocotrienol acetate, beta-tocotrienol acetate, delta-tocotrienol acetate, gamma-tocotrienol acetate, alpha-tocopherol succinate, beta-tocopherol succinate, gamma-tocopherol succinate, delta-tocopherol succinate, alpha-tocotrienol succinate, beta-tocotrienol succinate, delta-tocotrienol succinate, gamma-tocotrienol succinate, mixed tocopherols, vitamin E TPGS, derivatives, analogs and pharmaceutically acceptable salts thereof.

FIGS. 1 through 8C, wherein like parts are designated by like reference numerals throughout, illustrate an example embodiment of a non-polymeric biological and physical oil barrier layer according to the present invention. Although the present invention will be described with reference to the example embodiments illustrated in the figures, it should be understood that many alternative forms can embody the present invention. One of ordinary skill in the art will additionally appreciate different ways to alter the parameters of the embodiments disclosed, such as the size, shape, or type of elements or materials, in a manner still in keeping with the spirit and scope of the present invention.

FIG. 1 illustrates a non-polymeric biological oil barrier layer 10 in accordance with one embodiment of the present invention. The barrier layer 10 is flexible, to the extent that it can be placed in a flat, curved, or rolled, configuration within a patient. The barrier layer 10 is implantable, for both short term and long term applications. Depending on the particular formulation of the barrier layer 10, the barrier layer 10 will be present after implantation for a period of hours to days, or possibly months.

The barrier layer 10 is formed of an oil component. The oil component can be either an oil, or an oil composition. The oil component can be a naturally occurring oil, such as fish oil, cod liver oil, cranberry oil, or other oils having desired characteristics. One example embodiment of the present invention makes use of a fish oil in part because of the high content of omega-3 fatty acids, which provide healing support for damaged tissue, as discussed below. The fish oil also serves as an anti-adhesion agent. In addition, the fish oil maintains anti-inflammatory or non-inflammatory properties as well. The present invention is not limited to formation of the film with fish oil as the naturally occurring oil. However, the following description makes reference to the use of fish oil as one example embodiment. Other naturally occurring oils can be utilized in accordance with the present invention as described herein.

It should be noted that as utilized herein, the term fish oil fatty acid includes but is not limited to omega-3 fatty acid, fish oil fatty acid, free fatty acid, monoglycerides, di-glycerides, or triglycerides, esters of fatty acids, or a combination thereof. The fish oil fatty acid includes one or more of arachidic acid, gadoleic acid, arachidonic acid, eicosapentaenoic acid, docosahexaenoic acid or derivatives, analogs and pharmaceutically acceptable salts thereof. Furthermore, as utilized herein, the term free fatty acid includes but is not limited to one or more of butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, lignoceric acid, analogs and pharmaceutically acceptable salts thereof. The naturally occurring oils, including fish oil, are cured as described herein to form a hydrophobic cross-linked gel, creating the barrier layer 10.

It should further be noted that FIG. 1 represents merely one embodiment of the barrier layer 10. The barrier layer 10 serves as a biological oil barrier and, depending on degree of cure, can also serve as a physical barrier, as depicted. The biological oil barrier is represented by the application of the fatty acid based oil, such as fish oil, onto a medical device. Such a configuration provides a biological oil barrier layer that provides a non-inflammatory or anti-inflammatory barrier coating. Using a number of different methods as described below, the biological oil can be cured to create a non-polymeric cross-linked gel. In the instance of the medical device taking the form of a surgical mesh, the biological oil can be cured to the extent that the cells or pores of the mesh are substantially or completely bridged by the cured biological oil creating a physical barrier. With such a configuration there remains some biological oil that is not cured but is interdispersed within the cured oil and maintains the biological oil barrier layer as well. Thus, substantial curing creates both a biological oil barrier layer and a physical barrier. The physical barrier provides anti-adhesive properties of the barrier as discussed herein. Additional embodiments can include the provision of the substantially cured oil forming the biological oil barrier layer with physical layer, and then a subsequent application of the biological oil as a top coat. This creates a more substantial biological oil barrier layer supported by the combination biological oil barrier layer and physical barrier layer.

One aspect of the barrier layer 10 mentioned above is that it has anti-adhesion characteristics or properties. By anti-adhesion, what is meant is a characteristic whereby the incidence, extent, and severity of postoperative adhesions, or other lacerations or tissue injuries, between different tissues and organs is reduced. The anti-adhesion characteristic results from the materials used to form the barrier layer 10.

More specifically, the barrier layer 10 provides a lubricious and/or anti-adhesive surface against tissue. The barrier layer 10 itself, in its substantially cured configuration, can provide a physical anti-adhesion barrier between two sections of tissue, or the barrier layer 10 can form an anti-adhesion surface on a medical device, such as the mesh 40. The use of the naturally occurring oil, such as fish oil, provides extra lubrication to the surface of the medical device, which helps to reduce injury. With less injury, there is less of an inflammatory response, and less healing required. The biological oil barrier created by the fatty acid oil derived barrier layer likewise provides anti-inflammatory properties, thus reducing the occurrence of inflammatory response and also adhesions due to inflammation. The oily surface of the barrier layer 10 provides the anti-adhesion characteristics. One of ordinary skill in the art will appreciate that different oils will have different anti-adhesive properties, and the oils can be modified to be more liquefied or more solid or waxy, as desired. Accordingly, the degree of anti-adhesive properties offered by the barrier layer 10 can vary. The modification of the oils from a more liquid physical state to a more solid, but still flexible, physical state is implemented through the curing process. As the oils are cured, especially in the case of fatty acid-based oils such as fish oil, cross-links form creating a gel. As the curing process is performed over increasing time durations and/or increasing temperature or intensity conditions, more cross-links form transitioning the gel from a relatively liquid gel to a relatively solid-like, but still flexible, gel structure.

Another aspect of the present invention is that the barrier layer 10 is formed of the bio-absorbable material, such as naturally occurring fish oil, in accordance with the example embodiment described herein. The bio-absorbable properties of the naturally occurring oil enable the barrier layer 10 to be absorbed by the cells of the body tissue (i.e., bio-absorbable). In example embodiments of the present invention, the bio-absorbable barrier layer contains lipids, many of which originate as triglycerides. It has previously been demonstrated that triglyceride byproducts, such as partially hydrolyzed triglycerides and fatty acid molecules can integrate into cellular membranes and enhance the solubility of drugs into the cell. Whole triglycerides are known not to enhance cellular uptake as well as partially hydrolyzed triglyceride, because it is difficult for whole triglycerides to cross cell membranes due to their relatively larger molecular size. Vitamin E compounds can also integrate into cellular membranes resulting in decreased membrane fluidity and cellular uptake.

Compounds that move too rapidly through a tissue may not be effective in providing a sufficiently concentrated dose in a region of interest. Conversely, compounds that do not migrate in a tissue may never reach the region of interest. Cellular uptake enhancers such as fatty acids and cellular uptake inhibitors such as alpha-tocopherol can be used alone or in combination to provide an effective transport of a given compound to a given region or location. Both fatty acids and alpha-tocopherol are accommodated by the barrier layer of the present invention described herein. Accordingly, fatty acids and alpha-tocopherol can be combined in differing amounts and ratios to contribute to a barrier layer in a manner that provides control over the cellular uptake characteristics of the barrier layer and any therapeutic agents mixed therein.

For example, the amount of alpha-tocopherol can be varied in the barrier layer. Alpha-tocopherol is known to slow autoxidation in fish oil by reducing hydroperoxide formation, which results in a decrease in the amount of cross-linking in cured fish oil. In addition alpha-tocopherol can be used to increase solubility of drugs in the fish oil forming the barrier layer. Thus, varying the amount of alpha-tocopherol present in the barrier layer can impact the resulting formation. Alpha-tocopherol can actually protect the therapeutic drug during curing, which increases the resulting drug load in the barrier layer after curing. Furthermore, with certain therapeutic drugs, the increase of alpha-tocopherol in the barrier layer serves to slow and extend drug release due to the increased solubility of the drug in the alpha-tocopherol component of the barrier layer. This reflects the cellular uptake inhibitor functionality of alpha-tocopherol, in that the uptake of the drug is slowed and extended over time.

It should further be emphasized that the bio-absorbable nature of the barrier layer results in the barrier layer 10 being completely absorbed over time by the cells of the body tissue. There are no substances in the barrier layer, or break down products of the barrier layer, that induce an inflammatory response. The barrier layer 10 is generally composed of, or derived from, omega-3 fatty acids bound to triglycerides, potentially also including a mixture of free fatty acids and vitamin E (alpha-tocopherol). The triglycerides are broken down by lipases (enzymes) which result in free fatty acids that can than be transported across cell membranes. Subsequently, fatty acid metabolism by the cell occurs to metabolize any substances originating with the barrier layer. The bio-absorbable nature of the barrier layer of the present invention results in the barrier layer being absorbed over time, leaving only an underlying delivery or other medical device structure that is biocompatible. There is no foreign body inflammatory response to the bio-absorbable barrier layer.

Although the present invention is bio-absorbable to the extent that the barrier layer 10 experiences the uptake into or through body tissues, in the specific embodiment described herein formed using naturally occurring oils, the exemplar oils are also lipid based oils. The lipid content of the oils provides a highly bio-absorbable barrier layer 10. More specifically, there is a phospholipids layer in each cell of the body tissue. The fish oil, and equivalent oils, contain lipids as well. There is a lipophilic action that results where the lipids are attracted by each other in an effort to escape the aqueous environment surrounding the lipids.

A further aspect of the barrier layer 10 is that the specific type of oil can be varied, and can contain elements beneficial to healing. The barrier layer also provides a natural scaffold for cellular growth and remodeling with clinical applications in general surgery, spinal repair, orthopedic surgeries, tendon and ligament repairs, gynecological and pelvic surgeries, and nerve repair applications. The addition of therapeutic agents to the films used in these applications can be utilized for additional beneficial effects, such as pain relief or infection minimization. In addition, non-surgical applications include external wound care, such as a treatment for burns or skin ulcers, without therapeutics as a clean, non-permeable, non-adhesive, anti-inflammatory, non-inflammatory dressing, or with added therapeutics for additional beneficial effects. The film may also be used as a transdermal drug delivery patch.

The process of wound healing involves tissue repair in response to injury and it encompasses many different biologic processes, including epithelial growth and differentiation, fibrous tissue production and function, angiogenesis, and inflammation. The inventive cross-linked gel has been shown in an animal model not to produce an inflammatory response, but still provide excellent cellular overgrowth with little to no fibrous capsule formation. Accordingly, the cross-linked gel provides an excellent material suitable for wound healing applications.

Another aspect of the barrier layer 10 mentioned above is that the barrier layer 10 can contain therapeutic agents for delivery to the body tissue. Therapeutic agents have been delivered to a targeted location in a human utilizing a number of different methods in the past. For example, agents may be delivered nasally, transdermally, intravenously, orally, or via other conventional methods. Delivery may vary by release rate (i.e., quick release or slow release). Delivery may also vary as to how the drug is administered. Specifically, a drug may be administered locally to a targeted area, or administered systemically.

As utilized herein, the phrase "therapeutic agent(s)" refers to a number of different drugs or agents available, as well as future agents that may be beneficial for use with the barrier layer of the present invention. Therapeutic agents can be added to the barrier layer 10, and/or the medical device in combination with the barrier layer 10 as discussed herein. The therapeutic agent component can take a number of different forms including anti-oxidants, anti-inflammatory agents, anti-coagulant agents, drugs to alter lipid metabolism, anti-proliferatives, anti-neoplastics, tissue growth stimulants, functional protein/factor delivery agents, anti-infective agents, anti-imaging agents, anesthetic agents, therapeutic agents, tissue absorption enhancers, anti-adhesion agents, germicides, anti-septics, analgesics, prodrugs, and any additional desired therapeutic agents such as those listed in Table 1 below.

TABLE #1

| CLASS | EXAMPLES |
| --- | --- |
| Antioxidants | Alpha-tocopherol, lazaroid, probucol, phenolic antioxidant, resveretrol, AGI-1067, vitamin E |
| Antihypertensive Agents | Diltiazem, nifedipine, verapamil |
| Antiinflammatory Agents | Glucocorticoids (e.g. dexamethazone, methylprednisolone), leflunomide, NSAIDS, ibuprofen, acetaminophen, hydrocortizone acetate, hydrocortizone sodium phosphate, macrophage-targeted bisphosphonates |

TABLE #1-continued

| CLASS | EXAMPLES |
|---|---|
| Growth Factor Antagonists | Angiopeptin, trapidil, suramin |
| Antiplatelet Agents | Aspirin, dipyridamole, ticlopidine, clopidogrel, GP IIb/IIIa inhibitors, abciximab |
| Anticoagulant Agents | Bivalirudin, heparin (low molecular weight and unfractionated), wafarin, hirudin, enoxaparin, citrate |
| Thrombolytic Agents | Alteplase, reteplase, streptase, urokinase, TPA, citrate |
| Drugs to Alter Lipid Metabolism (e.g. statins) | Fluvastatin, colestipol, lovastatin, atorvastatin, amlopidine |
| ACE Inhibitors | Elanapril, fosinopril, cilazapril |
| Antihypertensive Agents | Prazosin, doxazosin |
| Antiproliferatives and Antineoplastics | Cyclosporine, cochicine, mitomycin C, sirolimus micophenonolic acid, rapamycin, everolimus, tacrolimus, paclitaxel, QP-2, actinomycin, estradiols, dexamethasone, methatrexate, cilostazol, prednisone, cyclosporine, doxorubicin, ranpirnas, troglitzon, valsarten, pemirolast, C-MYC antisense, angiopeptin, vincristine, PCNA ribozyme, 2-chloro-deoxyadenosine |
| Tissue growth stimulants | Bone morphogeneic protein, fibroblast growth factor |
| Promotion of hollow organ occlusion or thrombosis | Alcohol, surgical sealant polymers, polyvinyl particles, 2-octyl cyanoacrylate, hydrogels, collagen, liposomes |
| Functional Protein/Factor delivery | Insulin, human growth hormone, estradiols, nitric oxide, endothelial progenitor cell antibodies |
| Second messenger targeting | Protein kinase inhibitors |
| Angiogenic | Angiopoetin, VEGF |
| Anti-Angiogenic | Endostatin |
| Inhibation of Protein Synthesis/ECM formation | Halofuginone, prolyl hydroxylase inhibitors, C-proteinase inhibitors |
| Antiinfective Agents | Penicillin, gentamycin, adriamycin, cefazolin, amikacin, ceftazidime, tobramycin, levofloxacin, silver, copper, hydroxyapatite, vancomycin, ciprofloxacin, rifampin, mupirocin, RIP, kanamycin, brominated furonone, algae byproducts, bacitracin, oxacillin, nafcillin, floxacillin, clindamycin, cephradin, neomycin, methicillin, oxytetracycline hydrochloride, Selenium. |
| Gene Delivery | Genes for nitric oxide synthase, human growth hormone, antisense oligonucleotides |
| Local Tissue perfusion | Alcohol, H2O, saline, fish oils, vegetable oils, liposomes |
| Nitric oxide Donor Derivatives | NCX 4016 - nitric oxide donor derivative of aspirin, SNAP |
| Gases | Nitric oxide, compound solutions |
| Imaging Agents | Halogenated xanthenes, diatrizoate meglumine, diatrizoate sodium |
| Anesthetic Agents | Lidocaine, benzocaine |
| Descaling Agents | Nitric acid, acetic acid, hypochlorite |
| Anti-Fibrotic Agents | Interferon gamma-1b, Interluekin-10 |
| Immunosuppressive/Immunomodulatory Agents | Cyclosporine, rapamycin, mycophenolate motefil, leflunomide, tacrolimus, tranilast, interferon gamma-1b, mizoribine |
| Chemotherapeutic Agents | Doxorubicin, paclitaxel, tacrolimus, sirolimus, fludarabine, ranpirnase |
| Tissue Absorption Enhancers | Fish oil, squid oil, omega 3 fatty acids, vegetable oils, lipophilic and hydrophilic solutions suitable for enhancing medication tissue absorption, distribution and permeation |
| Anti-Adhesion Agents | Hyaluronic acid, human plasma derived surgical sealants, and agents comprised of hyaluronate and carboxymethylcellulose that are combined with dimethylaminopropyl, ehtylcarbodimide, hydrochloride, PLA, PLGA |
| Ribonucleases | Ranpirnase |
| Germicides | Betadine, iodine, sliver nitrate, furan derivatives, nitrofurazone, benzalkonium chloride, benzoic acid, salicylic acid, hypochlorites, peroxides, thiosulfates, salicylanilide |
| Antiseptics | Selenium |
| Analgesics | Bupivicaine, naproxen, ibuprofen, acetylsalicylic acid |

Some specific examples of therapeutic agents useful in the anti-restenosis realm include cerivastatin, cilostazol, fluvastatin, lovastatin, paclitaxel, pravastatin, rapamycin, a rapamycin carbohydrate derivative (for example, as described in US Patent Application Publication 2004/0235762), a rapamycin derivative (for example, as described in U.S. Pat. No. 6,200,985), everolimus, seco-rapamycin, seco-everolimus, and simvastatin. With systemic administration, the therapeutic agent is administered orally or intravenously to be systemically processed by the patient. However, there are drawbacks to a systemic delivery of a therapeutic agent, one of which is that the therapeutic agent travels to all portions of the patient's body and can have undesired effects at areas not targeted for treatment by the therapeutic agent. Furthermore, large doses of the therapeutic agent only amplify the undesired effects at non-target areas. As a result, the amount of therapeutic agent that results in application to a specific targeted location in a patient may have to be reduced when administered systemically to reduce complications from toxicity resulting from a higher dosage of the therapeutic agent.

Accordingly, an alternative to the systemic administration of a therapeutic agent is the use of a targeted local therapeutic agent delivery approach. With local delivery of a therapeutic agent, the therapeutic agent is administered using a medical device or apparatus, directly by hand, or sprayed on the tissue, at a selected targeted tissue location of the patient that requires treatment. The therapeutic agent emits, or is otherwise delivered, from the medical device apparatus, and/or carrier, and is applied to the targeted tissue location. The local delivery of a therapeutic agent enables a more concentrated and higher quantity of therapeutic agent to be delivered directly at the targeted tissue location, without having broader systemic side effects. With local delivery, the therapeutic agent that escapes the targeted tissue location dilutes as it travels to the remainder of the patient's body, substantially reducing or eliminating systemic side effects.

Targeted local therapeutic agent delivery using a medical device can be further broken into two categories, namely, short term and long term ranging generally within a matter of seconds or minutes to a few days or weeks to a number of months. Typically, to achieve the long term delivery of a therapeutic agent, the therapeutic agent must be combined with a delivery agent, or otherwise formed with a physical impediment as a part of the medical device, to slow the release of the therapeutic agent.

Prior attempts to create films and drug delivery platforms, such as in the field of stents, primarily make use of high molecular weight synthetic polymer based materials to provide the ability to better control the release of the therapeutic agent. Essentially, the polymer in the platform releases the drug or agent at a predetermined rate once implanted at a location within the patient. Regardless of how much of the therapeutic agent would be most beneficial to the damaged tissue, the polymer releases the therapeutic agent based on properties of the polymer. Accordingly, the effect of the therapeutic agent is substantially local at the surface of the tissue making contact with the medical device having the coating. In some instances the effect of the therapeutic agent is further localized to the specific locations of, for example, stent struts or mesh pressed against the tissue location being treated. These prior approaches can create the potential for a localized toxic effect.

The barrier layer 10 of the present invention, however, makes use of the natural oils to form a non-polymeric natural oil based therapeutic agent delivery platform, if desired. Furthermore, the barrier layer 10 can be formed in a manner that creates the potential for controlled long term release of a therapeutic agent, while still maintaining the benefits of the natural oil component of the barrier layer 10.

More specifically, it is known that oil that is oxygenated becomes a waxy solid. Attempts have been made to convert the polyunsaturated oils into a wax or solid to allow the oil to adhere to a device for a longer period of time. One such approach applies the oil to the medical device and allows the oil to dry.

With the present invention, and in the field of soft tissue applications, and in part because of the lipophilic mechanism enabled by the bio-absorbable lipid based barrier layer 10 of the present invention, the uptake of the therapeutic agent is facilitated by the delivery of the therapeutic agent to the cell membrane by the bio-absorbable barrier layer 10. Further, the therapeutic agent is not freely released into the body fluids, but rather, is delivered directly to the cells and tissue. In prior configurations using polymer based coatings, the drugs were released at a rate regardless of the reaction or need for the drug on the part of the cells receiving the drug.

In addition, when the oil provided to form the barrier layer 10 is a naturally occurring oil containing the omega-3 fatty acids (including DHA and EPA), the process for forming the barrier layer 10 can be tailored to avoid causing detrimental effects to the beneficial properties of the omega-3 fatty acids, or at least effects too detrimental to have any lasting effect. As described herein, certain properties of the fatty acids may lose their effectiveness, however other desired properties are maintained. If there is no concern for maintaining the beneficial effects, the curing and other steps leading to the formation of the barrier layer 10 can include steps that may reduce some of the beneficial properties of the omega-3 fatty acids, as understood by one of ordinary skill in the art. Example embodiments illustrating the formation and different configurations of the barrier layer 10 are provided herein.

To summarize, the barrier layer 10 of the present invention serves as a non-polymeric biological oil barrier layer and can also serve as a physical barrier layer if sufficiently cured. In accordance with the example embodiments described herein, the barrier layer is formed of a non-polymeric cross-linked gel, which can be derived from fatty acid compounds. The fatty acids include omega-3 fatty acids when the oil utilized to form the barrier layer is fish oil or an analog or derivative thereof. As liquid fish oil is heated, autoxidation occurs with the absorption of oxygen into the fish oil to create hydroperoxides in an amount dependent upon the amount of unsaturated ($C=C$) sites in the fish oil. However, the ($C=C$) bonds are not consumed in the initial reaction. Concurrent with the formation of hydroperoxides is the isomerization of ($C=C$) double bonds from cis to trans in addition to double bond conjugation. It has been demonstrated that hydroperoxide formation increases with temperature. Heating of the fish oil allows for cross-linking between the fish oil unsaturated chains using a combination of peroxide (C—O—O—C), ether (C—O—C), and hydrocarbon (C—C) bridges. The formation of the cross-links results in gelation of the barrier layer after the ($C=C$) bonds have substantially isomerized into the trans configuration. The ($C=C$) bonds can also form C—C cross-linking bridges in the glyceride hydrocarbon chains using a Diels-Alder Reaction. In addition to solidifying the barrier layer through cross-linking, both the hydroperoxide and ($C=C$) bonds can undergo secondary reactions converting them into lower molecular weight secondary oxidation byproducts including aldehydes, ketones, alcohols, fatty acids, esters, lactones, ethers, and hydrocarbons.

Accordingly, the barrier layer non-polymeric cross-linked gel derived from fatty acid compounds, such as those of fish oil, includes a cross-linked structure of triglyceride and fatty acid molecules in addition to free and bound glycerol, monoglyceride, diglyceride, and triglyceride, fatty acid, anhydride, lactone, aliphatic peroxide, aldehyde, and ketone molecules. There are a substantial amount of ester bonds remaining after curing in addition to peroxide linkages forming the majority of the cross-links in the gel. The barrier layer degrades into fatty acid, short and long chain alcohol, and glyceride molecules, which are all non-inflammatory and likewise consumable by cells in the soft tissue to which the barrier layer is applied. Thus, the barrier layer is bio-absorbable.

Figure 2A:
FIGS. 2A, 2B, and 2C are cross-sectional views of the barrier layer in accordance with one aspect of the present invention.
Figure 2B:
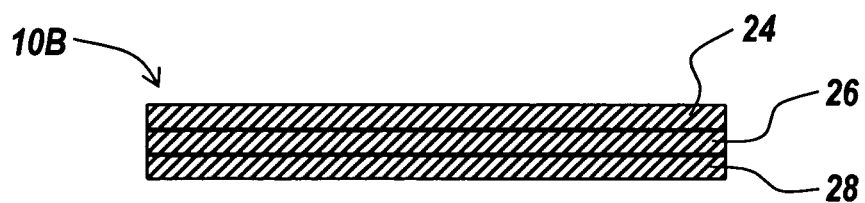
Figure 2C:
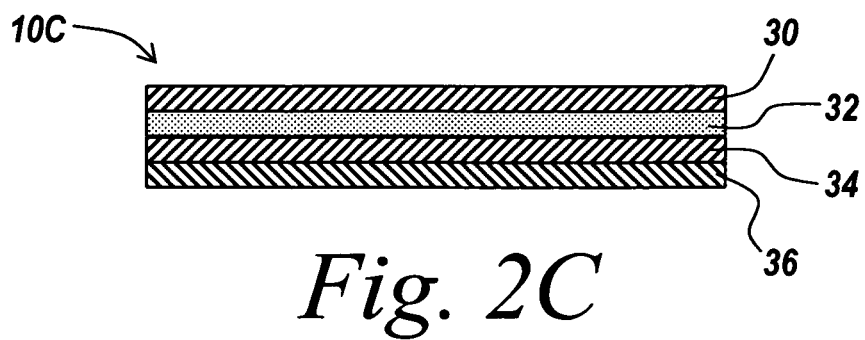
Figure 3A:
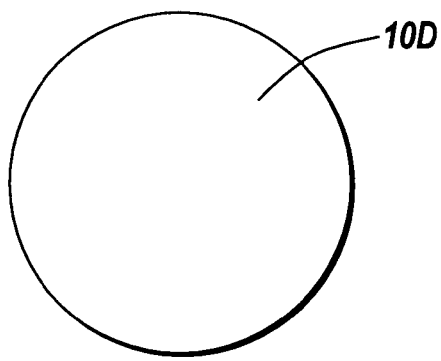
FIGS. 3A, 3B, 3C, 3D, 3E, and 3F are diagrammatic views of the barrier layer in accordance with another aspect of the present invention.
Figure 3B:
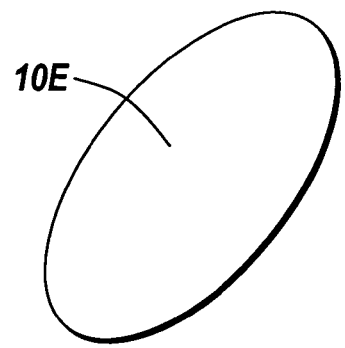
Figure 3C:
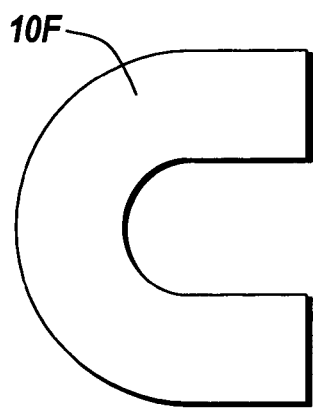
Figure 3D:
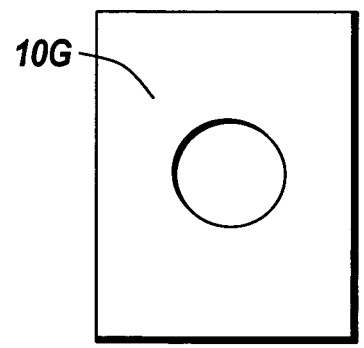
Figure 3E:
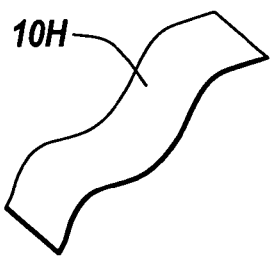
Figure 3F:
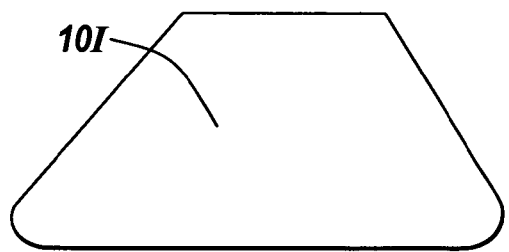

FIGS. 2A, 2B, and 2C illustrate side views of multiple different embodiments of the barrier layer 10 when cured into a flexible cross-linked gel. In FIG. 2A, a barrier layer 10A is shown having two tiers, a first tier 20 and a second tier 22. The first tier 20 and the second tier 22 as shown are formed of different materials. The different materials can be different forms of fish oil, different naturally occurring oils other than fish oil, or therapeutic components as will be discussed later herein. The different materials bind together to form the barrier layer 10A.

FIG. 2B shows a barrier layer 10B having a first tier 24, a second tier 26, and a third tier 28. In the embodiment shown, each of the tiers 24, 26, and 28 is formed of the same material. The plurality of tiers indicates the ability to create a thicker barrier layer 10 if desired. The greater the number of tiers, the thicker the resulting film. The thickness of the barrier layer 10 can have an effect on the overall strength and durability of the barrier layer 10. A thicker film is generally stronger and more durable. In addition, the thickness of the barrier layer 10 can also affect the duration of time that the barrier layer 10 lasts after implantation. A thicker barrier layer 10 provides more material to be absorbed by the body, and thus will last longer than a thinner barrier layer 10. One of ordinary skill in the art will appreciate that the thickness of the barrier layer 10 can vary both by varying the thickness of each tier 24, 26, and 28, and by varying the number of tiers 24, 26, and 28. Accordingly, the present invention is not limited to the particular layer combinations illustrated.

FIG. 2C shows another barrier layer 10C, having four tiers, a first tier 30, a second tier 32, a third tier 34, and a fourth tier 36. In this example embodiment, the first tier 30 and the third tier 34 are formed of the same material, while the second tier 32 and the fourth tier 36 are formed of a material different from each other and different from that of the first tier 30 and the third tier 34. Accordingly, this embodiment illustrates the ability to change the number of tiers, as well as the material used to form each of the tiers 30, 32, 34, and 36. Again, the different materials can be derived from different forms of fish oil, different naturally occurring oils other than fish oil, or therapeutic components as will be discussed later herein.

FIGS. 3A through 3F show additional embodiments or configurations of the barrier layer 10. The embodiments include barrier layer 10D in a circular configuration, barrier layer 10E in an oval configuration, barrier layer 10F in a U-bend configuration, barrier layer 10G in a square configuration having a circular aperture, barrier layer 10H in a wave configuration, and barrier layer 10I in an irregular shape configuration. Each of the configurations of the barrier layer 10D through 10I represent different types of configurations. The configurations illustrated are by no means the only possible configurations for the barrier layer 10. One of ordinary skill in the art will appreciate that the specific shape or configuration of the barrier layer 10 can vary as desired. A more prevalent configuration is the rectangular or oblong configuration of FIG. 1. However, FIGS. 3A through 3F illustrate a number of different alternative embodiments, and indicate some of the many possible configurations.

FIG. 4 is a flowchart illustrating one example method for the formation of the barrier layer 10. A surface is provided having a release agent (step 100). The surface can be prepared by the application of the release agent, or the release agent can be pre-existing. The release agent can be a number of different solutions, including for example, polyvinyl alcohol (PVA). The release agent can be applied in a number of different ways as well, including but not limited to spraying, dipping, coating, painting, and the like. It should be noted that the release agent can be applied to the surface immediately prior to the remaining steps or well in advance of the remaining steps, so long as when the remaining steps are executed there is a release agent on the surface. It should further be noted that the need of a release agent can be eliminated if the surface itself has inherent characteristics similar to one having a release agent. Specifically, the surface can instead have a Teflon® coating, or other similar more permanent release surface. In such an instance, there is no need for a release agent, or subsequent removal of the release agent from the barrier layer formed.

An oil component is applied to the surface on top of the release agent (step 102). As noted previously, the oil component can be a naturally occurring oil, such as fish oil, cod liver oil, cranberry oil, or other oils having desired characteristics. In addition, the oil component can be an oil composition, meaning a composition containing oil in addition to other substances. For example, the oil composition can be formed of the oil component in addition to a solvent and/or a preservative. Solvents can include a number of different alternatives, including ethanol or N-Methyl-2-Pyrrolidone (NMP). The preservative can also include a number of different alternatives, including vitamin E. One of ordinary skill in the art will appreciate that there are a number of different solvents and preservatives available for use with the oil component to form the oil composition, and as such the present invention is not limited to only those listed in the examples herein. The solvent can be useful to alter the physical properties of the oil, as well as prepare the oil for combination with a therapeutic agent as described below. The preservative can also be useful in altering the physical properties of the oil component, as well as protecting some of the beneficial properties of the oil component during certain curing processes. Such beneficial properties include the healing and anti-inflammatory characteristics previously mentioned.

The oil component can be combined with one or more therapeutic agents to form an oil composition. Thus, if the added therapeutic benefit of a particular therapeutic agent or agents is desired, the therapeutic agent(s) can be added to the oil component prior to application to the surface, along with the oil component during application to the surface (including mixing with the oil component prior to application), or after the oil component has been applied (step 104). The different alternatives for adding the therapeutic agent(s) are determined in part based on the desired effect and in part on the particular therapeutic agent(s) being added. Some therapeutic agents may have reduced effect if present during a subsequent curing step. Some therapeutic agents may be more useful intermixed with the oil component to extend the release period, or applied to the surface of the oil component, resulting in a faster release because of increased exposure. One of ordinary skill in the art will appreciate that a number of different factors, such as those listed above in addition to others, can influence when in the process the therapeutic agent is added to the oil component, or the barrier layer 10. Accordingly, the present invention is not limited to the specific combinations described, but is intended to anticipate all such possible variations for adding the therapeutic agent(s).

For example, if 80% of a therapeutic agent is rendered ineffective during curing, the remaining 20% of therapeutic agent, combined with and delivered by the barrier can be efficacious in treating a medical disorder, and in some cases have a relatively greater therapeutic effect than the same quantity of agent delivered with a polymeric or other type of coating or barrier. This result can be modified with the variance of alpha-tocopherol to protect the therapeutic agent during the curing process, and then slow and extend the delivery of the therapeutic agent during absorption of the barrier layer into the tissue.

The oil component (or composition if mixed with other substances) is then hardened into the barrier layer 10 (step 106). The step of hardening can include hardening, or curing, such as by introduction of UV light, heat, oxygen or other reactive gases, chemical curing, or other curing or hardening method. The purpose of the hardening or curing is to transform the more liquid consistency of the oil component or oil composition into a more solid film, while still maintaining sufficient flexibility to allow bending and wrapping of the film as desired. However, the hardening process as described herein does not refer to or include the process of hydrogenation.

After the barrier layer 10 has formed, another determination is made as to whether therapeutic agents should be applied to the film. If desired, the therapeutic agent(s) is added to the barrier layer 10 (step 108). Subsequently, the barrier layer 10 is removed from the surface (step 110). Once again, there is opportunity to apply a therapeutic agent(s) to the barrier layer 10 on one or both sides of the barrier layer 10. If such therapeutic agent(s) is desired, the therapeutic agent(s) is applied (step 112). The additional therapeutic agent can also be applied in the form of a non-cured or minimally cured oil, such as fish oil. The oil can likewise include other therapeutic agents mixed therewith. The resulting structure of such an application forms the underlying barrier layer 10 that is cured to form the film, with a top coating of oil and potentially additional therapeutic agent layered on top. This structure enables the provision of a short term release of therapeutic from the oil top layer combined with a longer term release from the cured film, which takes more time to degrade.

After application of the therapeutic agent(s), or after the barrier layer 10 is removed from the surface, the barrier layer 10 is sterilized. The sterilization process can be implemented in a number of different ways. For example, sterilization can be implemented utilizing ethylene oxide, gamma radiation, E beam, steam, gas plasma, or vaporized hydrogen peroxide (VHP). One of ordinary skill in the art will appreciate that other sterilization processes can also be applied, and that those listed herein are merely examples of sterilization processes that result in a sterilization of the barrier layer 10, preferably without having a detrimental effect on the barrier layer.

It should be noted that the oil component or oil composition can be added multiple times to create multiple tiers in forming the barrier layer 10. For example, if a thicker barrier layer 10 is desired, additional tiers of the oil component or oil composition can be added after steps 100, 104, 106, 108, 110, or 112. Different variations relating to when the oil is hardened and when other substances are added to the oil are possible in a number of different process configurations. Accordingly, the present invention is not limited to the specific sequence illustrated. Rather, different combinations of the basic steps illustrated are anticipated by the present invention.

Figure 5A:
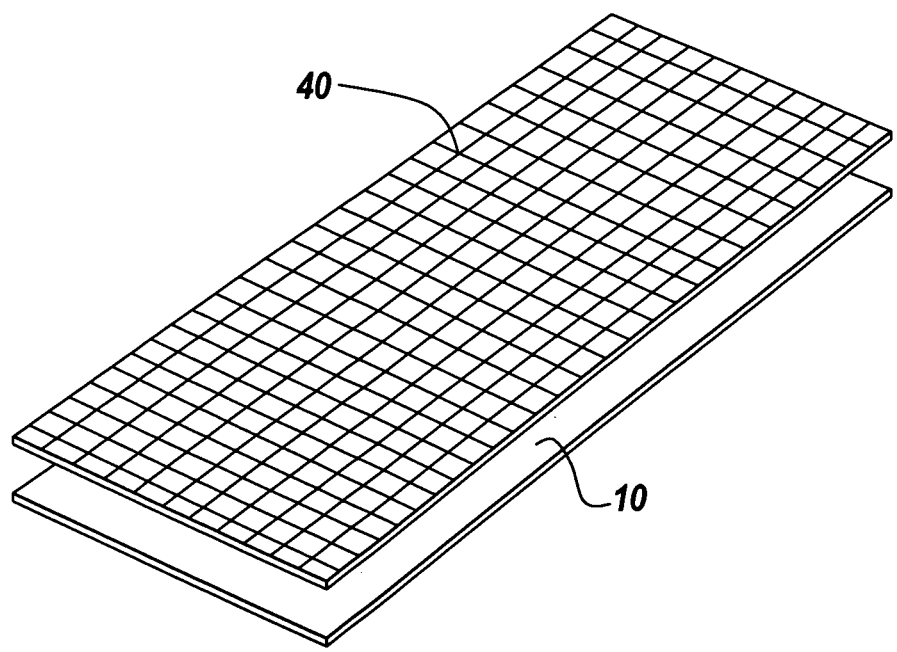
FIGS. 5A and 5B are perspective and cross-sectional views of the barrier layer in combination with a medical device, in accordance with one embodiment of the present invention.
Figure 5B:
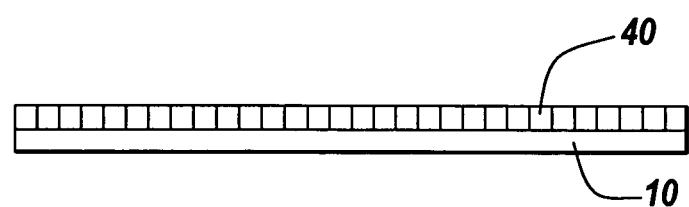

FIGS. 5A and 5B illustrate the barrier layer 10 and a medical device in the form of a mesh 40. In FIG. 5A, the barrier layer 10 and mesh 40 are shown in exploded view, while FIG. 5B shows the barrier layer 10 coupled with the mesh 40. The mesh 40 is merely one example medical device that can be coupled with the barrier layer 10. In the instance of the mesh 40, it can be useful to have one side of the mesh support a rougher surface to encourage tissue in-growth, and the other side of the mesh with an anti-adhesion, anti-inflammatory, and/or non-inflammatory surface to prevent the mesh from injuring surrounding tissue or causing inflammation. The coupling of the barrier layer 10 with the mesh 40 achieves such a device.

As understood by one of ordinary skill in the art, the properties of the mesh 40 and the barrier layer 10 can vary. There may be a requirement for the mesh 40 to have one side, or a portion of a side, that has anti-adhesion properties for a period of several days. Alternatively, multiple sides of the mesh 40 may be required to have anti-adhesion properties. As such, the barrier layer 10 can be applied to all sides, or portions of sides, or portions of one side of the mesh 40.

In addition, the requirement may be for the anti-adhesion properties to last several weeks, or even longer. Accordingly, the rate of degradation can also be varied by changing such properties as amount of cross-linking, thickness, and existence of additives, such as vitamin E compounds to achieve longer or shorter term anti-adhesion properties. In addition, there may be a desire to include a therapeutic agent to reduce inflammation, provide antibiotic therapy, or other therapeutic measures, in combination with the use of the mesh 40. Accordingly, the therapeutic agent(s) can be added to the barrier layer 10 to achieve the desired controlled release of the therapeutic agent after implantation. As previously described, combinations of cured oils top coated with lesser cured or non-cured oils and therapeutic agents can form the barrier layer 10.

The particular properties or characteristics of the mesh 40 are determined based on the desired use of the mesh 40. A common implementation is for the mesh 40 to be formed of a bio-compatible material, such as polypropylene, however other bio-compatible materials can be utilized, such as a mesh formed of the same or similar substance as the barrier layer 10 (i.e., oil based).

Figure 6:
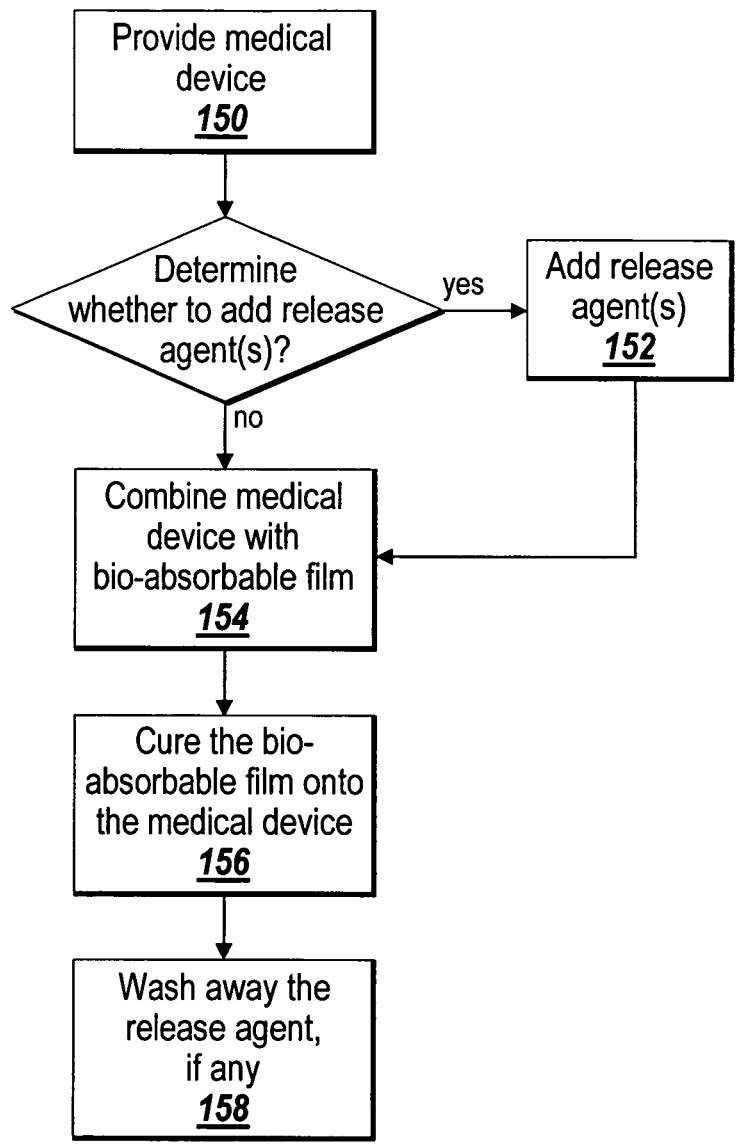
FIG. 6 is a flow chart illustrating a method of combining the barrier layer with a medical device, in accordance with one embodiment of the present invention.

FIG. 6 is a flowchart illustrating one example method for forming the mesh 40 and barrier layer 10 combination. The medical device is provided (step 150). The medical device can be, for example, the mesh 40.

A determination is made as to whether a release agent should be added to the medical device to aid in removing the device from its location (e.g., on a surface) after combination with the barrier layer 10. If a release agent is required, the release agent is applied to the medical device (step 152). An example release agent for such an application is polyvinyl alcohol.

The medical device is then combined with the barrier layer 10 (step 154). Depending on the particular medical device, the combination with the barrier layer 10 can be implemented more efficiently by either applying the barrier layer 10 to the medical device, or placing the medical device on the barrier layer 10. For example, in the case of the mesh 40, the mesh 40 can be placed on top of the barrier layer 10, or the barrier layer 10 can be placed on top of the mesh 40.

The medical device and the barrier layer are then cured to create a bond (step 156). The curing process can be one of several known processes, including but not limited to applying heat, or UV light, or chemical curing, to cure the barrier layer. After curing, if there is any release agent present, the release agent is washed away using water, or some other washing agent (step 158).

Figure 7:
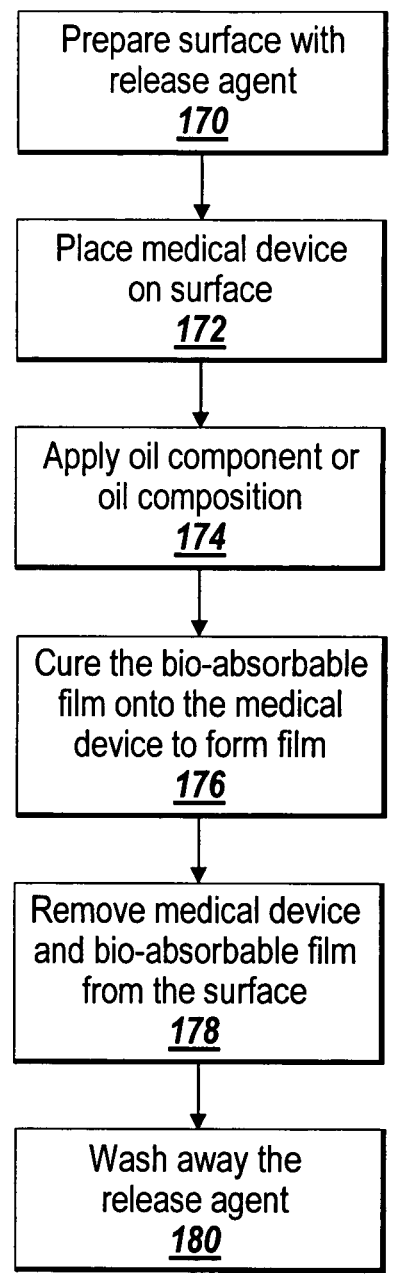
FIG. 7 is a flow chart illustrating another variation of the method of FIG. 6, in accordance with one embodiment of the present invention.

FIG. 7 is a flowchart illustrating another example method of forming a medical device with a barrier layer. A surface is prepared with a release agent, such as PVA (step 170). The medical device is placed on the surface (step 172). In the example embodiment, the medical device is the mesh 40.

The oil component or oil composition is applied to the medical device (step 174). In the instance of the mesh 40, the oil component or oil composition is poured or sprayed onto the mesh 40. The combined oil component/composition and mesh 40 are then cured (step 176) using methods such as application of heat, UV light, oxygen and other reactive gases, chemical cross-linker, or hardening processes, to form the barrier layer in combination with the mesh 40. The combined barrier layer and mesh are then removed from the surface (step 178) and the release agent is washed away (step 180).

As with the method of FIG. 6, if desired, a therapeutic agent can be added to the oil component or oil composition at any point along the process forming the combined barrier layer 10 and mesh 40, including being a component of the oil composition. As discussed previously, consideration must be given as to whether the therapeutic agent may be affected by the curing process, or other aspects of the process.

Furthermore, the formation of the oil composition can be done in accordance with different alternatives to the methods described. For example, prior to forming the barrier layer 10, a preservative and/or compatibilizer, such as Vitamin E can be mixed with the naturally occurring oil component to form the oil composition. A solvent can be mixed with a therapeutic agent, and then added to the naturally occurring oil to form the oil composition. The solvent can be chosen from a number of different alternatives, including ethanol or N-Methyl-2-Pyrrolidone (NMP). The solvent can later be removed with vacuum or heat.

In addition, it should again be noted that the oil component or oil composition can be added multiple times to create multiple tiers in forming the barrier layer 10. If a thicker barrier layer 10 is desired, additional tiers of the oil component or oil composition can be added after steps 174 and 176. Different variations relating to when the oil is hardened and when other substances are added to the oil are possible in a number of different process configurations. Accordingly, the present invention is not limited to the specific sequence illustrated. Rather, different combinations of the basic steps illustrated are anticipated by the present invention.

Depending on the type of therapeutic agent component added to the barrier layer 10, the resulting barrier layer 10 can maintain its bio-absorbable characteristics if the therapeutic agent component is also bio-absorbable.

The therapeutic agent component, as described herein, has some form of therapeutic or biological effect. The oil component or oil composition component can also have a therapeutic or biological effect. Specifically, the barrier layer 10 (and its oil constituents) enable the cells of body tissue of a patient to absorb the barrier layer 10 itself, rather than breaking down the film and disbursing by-products of the film for ultimate elimination by the patient's body.

As previously stated, and in accordance with embodiments of the present invention, the barrier layer 10 is formed of a naturally occurring oil, or composition including a naturally occurring oil, such as fish oil, cod liver oil, cranberry oil, and the like. A characteristic of the naturally occurring oil is that the oil includes lipids, which contributes to the lipophilic action described later herein, that is helpful in the delivery of therapeutic agents to the cells of the body tissue. In addition, the naturally occurring oil can include the essential omega-3 fatty acids in accordance with several embodiments of the present invention.

It should also be noted that the present description makes use of the mesh 40 as an example of a medical device that can be combined with the barrier layer 10 of the present invention. However, the present invention is not limited to use with the mesh 40. Instead, any number of other implantable medical devices can be combined with the barrier layer 10 in accordance with the teachings of the present invention. Such medical devices include catheters, grafts, balloons, prostheses, stents, other medical device implants, and the like. Furthermore, implantation refers to both temporarily implantable medical devices, as well as permanently implantable medical devices.

Figure 8A:
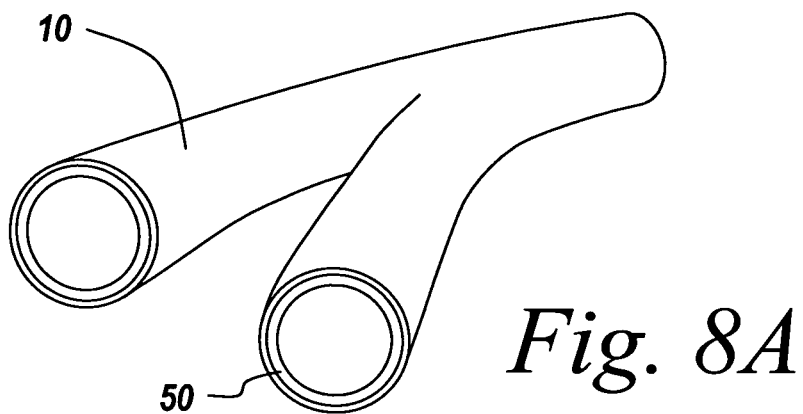
FIGS. 8A, 8B, and 8C are diagrammatic illustrations of the barrier coupled with various medical devices.
Figure 8B:
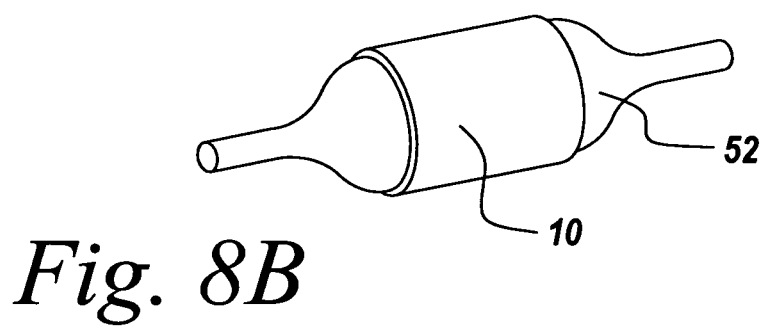
Figure 8C:
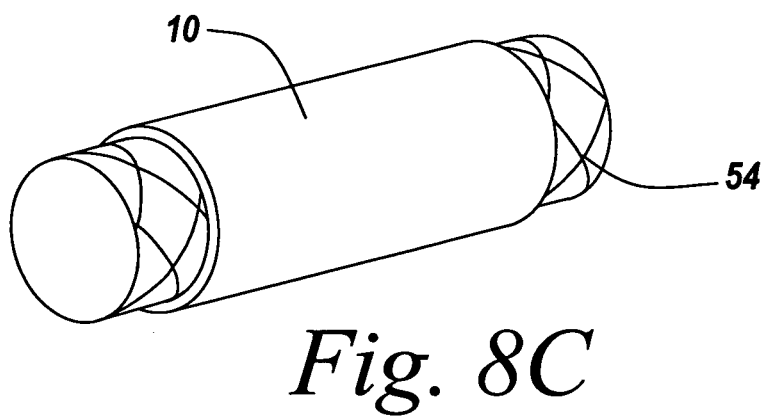

FIGS. 8A, 8B, and 8C illustrate some of the other forms of medical devices mentioned above in combination with the barrier layer 10 of the present invention. FIG. 8A shows a graft 50 with the barrier layer 10 coupled or adhered thereto. FIG. 8B shows a catheter balloon 52 with the barrier layer 10 coupled or adhered thereto. FIG. 8C shows a stent 54 with the barrier layer 10 coupled or adhered thereto. Each of the medical devices illustrated, in addition to others not specifically illustrated or discussed, can be combined with the barrier layer 10 using the methods described herein, or variations thereof. Accordingly, the present invention is not limited to the example embodiments illustrated. Rather the embodiments illustrated are merely example implementations of the present invention.

EXAMPLE #1

An embodiment of the present invention was implemented in a rat model to demonstrate the performance of the barrier layer of the present invention relative to other known surgical mesh devices. The devices were implanted in a rat to repair abdominal wall defects. Healing characteristics, adhesion formation and tenacity, and inflammatory response associated with these materials were compared.

A polypropylene mesh material (ProLite™) provided by Atrium Medical Corporation of Hudson, N.H., coated with one embodiment of the barrier layer described herein. The polypropylene mesh with barrier layer was compared with a bare polypropylene control mesh, and DualMesh® biomaterial provided by W. L. Gore & Associates, Inc.

Five samples of each mesh type were implanted according to a random schedule. On the day of surgery, the animals were anesthetized with an injection of 50 mg/kg Nembutal IP. The animal was prepped for surgery, and a midline abdominal incision was made. A portion of rectus muscle and fascia was removed leaving an approximately 20 mm×30 mm full thickness defect in the abdominal wall. Using 4-0 Prolene, the appropriate patch was sutured into place repairing the existing defect. An overlap of mesh was placed over the defect to ensure proper repair, with the mesh samples being 2.5 cm×3.5 cm in size. The mesh was placed such that the smoother side was toward the viscera in the case of the polypropylene mesh with barrier layer, and the appropriate side of the Gore DualMesh was also placed towards the viscera. Suture knots were made on the abdominal wall side of the implant rather than the visceral side as to not interfere with tissue attachment. The mesh was sutured around the entire perimeter to ensure adequate placement. The subdermal and subcutical layers were closed with Vicryl. The skin was closed using surgical staples. The animals received Buprenorphine for pain. The mesh was explanted at approximately 30 days.

Sample Explantation:

Approximately 30 days after implantation, the animals were again anesthetized for explant of the mesh samples. The skin staples were removed, and a vertical incision through the skin and subcutaneous tissue was made lateral to both the implantation site and patch. Through this incision, the implant was inspected and photos were taken to document adhesion formation. Upon gross examination, the same investigator evaluated each sample for adherent intraperitoneal tissues and assigned an adhesion grade to each sample (Jenkins S D, Klamer T W, Parteka J J, and Condon R E. A comparison of prosthetic materials used to repair abdominal wall defects. Surgery 1983; 94:392-8). In general, the adhesions were scored as: 0—no adhesions; 1—minimal adhesions that could be freed by gentle blunt dissection; 2—moderate adhesions that could be freed by aggressive blunt dissection; 3—dense adhesion that require sharp dissection.

Once the gross evaluation was complete, the mid-portion of the abdominal cavity was excised including the implant, and adhesive tissue not completely separated from the implant, and the overlying subcutaneous and skin. Sections were then fixed and processed for histological evaluation. The histology samples were stained with Hematoxylin and Eosin, Trichrome, GS1, and Vimentin.

Polypropylene Mesh Control:

These patches had a mean adhesion score of 2.1. Adhesions consisted of omentum, epididymal fat, and one had intestinal adhesions. Many of the adhesions were at the edges of the patch/tissue interface. The adhesions required aggressive blunt dissection to remove them. There was a moderate inflammatory response associated around the fibers of the mesh. There was a tight association of fat to the implant surface on the peritoneal cavity side, meaning the adhesions were not fully removed.

Gore DualMesh® Control:

Patches were entirely covered with adhesions. The adhesions consisted of epididymal fat, omentum and bowel. The mean adhesion score was 2.9. There was a capsule covering the entire patch that needed sharp dissection to free from material. Adhesions pulled free from capsule with blunt dissection. A moderate to severe inflammatory response was observed in association with the skin side of the implant. The thin fibrous capsule on the peritoneal side of the implant was avascular and in some implants was loosely adherent to associated tissue.

Polypropylene Mesh with Barrier Layer (Embodiment of Present Invention):

These patches had a mean adhesion score of 1.6. Adhesions included epididymal fat and some omentum. The adhesions dissociated from the patches relatively easily. There was a mild to minimal inflammatory response associated with the exposed polypropylene fibers of this material. Vimentin staining showed a layer of mesothelial cells formed on the tissue on the peritoneal cavity side of the implant.

The polypropylene mesh with barrier layer in accordance with one embodiment of the present invention showed good results in terms of adhesion minimization, tenacity of adhesions formed, and a low inflammatory response. The coated mesh product was also easy to handle, place, and suture for repair of an abdominal wall defect in this model.

The oil component itself, in the form of fish oil for example, can provide therapeutic benefits in the form of reduced inflammation, and improved healing, if the fish oil composition is not substantially modified during the process that takes the naturally occurring fish oil and forms it into the barrier layer 10. Some prior attempts to use natural oils as coatings have involved mixing the oil with a solvent, or curing the oil in a manner that destroys the beneficial aspects of the oil. The solvent utilized in the example barrier layer 10 embodiment of the present invention (NMP) does not have such detrimental effects on the therapeutic properties of the fish oil. Thus the benefits of the omega-3 fatty acids, and the EPA and DHA substances are substantially preserved in the barrier layer of the present invention.

Therefore, the barrier layer 10 of the present invention includes the bio-absorbable naturally occurring oil (i.e., fish oil). The barrier layer 10 is thus able to be absorbed by the cells of the body tissue. With the present invention, because of the lipophilic action enabled by the bio-absorbable lipid based barrier layer 10 of the present invention, the intake by the tissue cells of the barrier layer 10, and any therapeutic agent component, is substantially controlled by the cells themselves. In configurations using polymer based materials, the drugs were released at a rate regardless of the reaction or need for the drug on the part of the cells receiving the drug. With the barrier layer 10 of the present invention, the cells can intake as much of the barrier layer 10, and correspondingly the therapeutic agent, as is needed by the damaged cell requiring treatment.

In addition, the bio-absorbable nature of the barrier layer 10 results in the barrier layer 10 being completely absorbed over time by the cells of the body tissue. There is no break down of the barrier layer 10 into sub parts and substances that are inflammatory and are eventually distributed throughout the body and in some instances disposed of by the body, as is the case with biodegradable synthetic polymer coatings. The bio-absorbable nature of the barrier layer 10 of the present invention results in the barrier layer 10 being absorbed, leaving only the medical device structure, if the barrier layer 10 is not implanted alone. There is no inflammatory foreign body response to the barrier layer 10.

In addition, the barrier layer 10 provides a lubricious and/or anti-adhesive surface against tissue. The barrier layer 10 itself can provide an anti-adhesion barrier between two sections of tissue, or the barrier layer 10 can form an anti-adhesion surface on a medical device, such as the mesh 40. The use of the naturally occurring oil, such as fish oil, provides extra lubrication to the surface of the medical device, which helps to reduces injury. With less injury, there is less of an inflammatory response, and less healing required. Likewise the fatty acid derived cross-linked gel that makes up the barrier layer maintains anti-inflammatory properties which also substantially lowers the inflammatory response of the tissue. The reduced inflammation also reduces adhesions.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the invention, and exclusive use of all modifications that come within the scope of the appended claims is reserved. It is intended that the present invention be limited only to the extent required by the appended claims and the applicable rules of law.

What is claimed is:

1. An implantable medical device, comprising:
a surgical mesh structure; and
an anti-adhesion barrier layer and a biological oil barrier layer formed on at least a portion of the surgical mesh structure, wherein the anti-adhesion barrier layer comprises a cured fish oil that is hydrolysable by lipase, wherein the fish oil comprises eicosapentaenoic acid and docosahexanoic acid, wherein the cured oil comprises fatty acids and glycerides, wherein two or more of the fatty acids are cross-linked to each other by ester bonds in a substantially random configuration, wherein the anti-adhesion barrier layer is solid but flexible and serves as a physical barrier, and wherein the anti-adhesion barrier layer is bio-absorbable and degrades into non-inflammatory substances, and wherein the biological oil barrier layer comprises uncured fish oil.

2. The device of claim 1, wherein the anti-adhesion barrier layer and the biological barrier layer each comprises at least one therapeutic agent component.

3. The device of claim 2, wherein the therapeutic agent component comprises an agent selected from the group consisting of antioxidants, anti-inflammatory agents, anti-coagulant agents, drugs to alter lipid metabolism, anti-proliferatives, anti-neoplastics, tissue growth stimulants, functional protein/factor delivery agents, anti-infective agents, imaging agents, anesthetic agents, chemotherapeutic agents, tissue absorption enhancers, anti-adhesion agents, germicides, analgesics, prodrugs, and antiseptics.

4. The device of claim 1, wherein the anti-adhesion barrier layer comprises a plurality of tiers.

5. The device of claim 1, wherein the anti-adhesion barrier layer comprises a first tier configured on the mesh structure and a second tier configured on the first tier, wherein the first tier is cured to a greater extent than the second tier.

6. The device of claim 1, wherein the anti-adhesion barrier layer comprises a first tier configured on the mesh structure and a second tier configured on the first tier, wherein the second tier is cured to a greater extent than the first tier.

7. The device of claim 1, wherein the anti-adhesion barrier layer is configured to provide controlled release of a therapeutic agent component.

8. The device of claim 1, wherein the anti-adhesion barrier layer comprises the cured fish oil in combination with at least one component selected from a group of components consisting of uncured fish oil of the biological oil barrier layer, a therapeutic agent component, a solvent, and a preservative.

9. The device of claim 1, wherein the anti-adhesion barrier layer maintains anti-inflammatory properties.

10. The device of claim 1, wherein the anti-adhesion barrier layer comprises the uncured fish oil of the biological oil barrier layer interdispersed with the cured fish oil of the anti-adhesion barrier layer, such that the anti-adhesion barrier layer forms a cured cross-linked gel and together with the uncured fish oil forms a combined biological oil barrier and anti-adhesion barrier as a single layer on the medical device.

11. The device of claim 1, wherein the anti-adhesion barrier layer is configured on one side of the mesh structure.

12. The device of claim 1, wherein the anti-adhesion barrier layer is configured on a portion of one side of the mesh structure.

13. The device of claim 1, wherein the anti-adhesion barrier layer is configured on two sides of the mesh structure.

14. The device of claim 1, wherein the anti-adhesion barrier layer and the biological oil barrier layer each further comprises one or more of alpha tocopherol, beta-tocopherol, delta-tocopherol, gamma-tocopherol, alpha-tocotrienol, beta-tocotrienol, delta-tocotrienol, gamma-tocotrienol, alpha-tocopherol acetate, beta-tocopherol acetate, gamma-tocopherol acetate, delta-tocopherol acetate, alpha-tocotrienol acetate, betatocotrienol acetate, delta-tocotrienol acetate, gamma-tocotrienol acetate, alpha-tocopherol succinate, beta-tocopherol succinate, gamma-tocopherol succinate, delta-tocopherol succinate, alpha-tocotrienol succinate, beta-tocotrienol succinate, delta-tocotrienol succinate, gammatocotrienol succinate, mixed tocopherols, vitamin E TPGS, and pharmaceutically acceptable salts thereof.

15. The device of claim 1, wherein the biological oil barrier layer is disposed on the anti-adhesion barrier layer as a top coat.

16. An implantable barrier layer device, comprising:
a biocompatible mesh structure; and
an anti-adhesion barrier layer and a biological oil barrier layer formed on at least a portion of the mesh structure so that the anti-adhesion barrier layer covers a first side of the mesh but does not completely cover the other side of the mesh, wherein the anti-adhesion barrier layer comprises a heat-cured fish oil that is hydrolysable by lipase, wherein the fish oil comprises eicosapentaenoic acid and docosahexanoic acid, wherein the cured oil comprises fatty acids and glycerides, wherein two or more of the fatty acids are cross-linked to each other by ester bonds in a substantially random configuration, wherein the anti-adhesion barrier layer is in a solid state that is flexible, and wherein the anti-adhesion barrier layer is bio-absorbable and degrades into non-inflammatory substances, and wherein the biological oil barrier layer comprises uncured fish oil.

17. The device of claim 16, wherein the anti-adhesion barrier layer comprises at least one therapeutic agent component.

18. The device of claim 17, wherein the therapeutic agent component comprises an agent selected from the group consisting of antioxidants, anti inflammatory agents, anti-coagulant agents, drugs to alter lipid metabolism, anti-proliferatives, anti-neoplastics, tissue growth stimulants, functional protein/factor delivery agents, anti-infective agents, imaging agents, anesthetic agents, chemotherapeutic agents, tissue absorption enhancers, anti-adhesion agents, germicides, analgesics, prodrugs, and antiseptics.

19. The device of claim 16, wherein the anti-adhesion barrier layer comprises a plurality of tiers.

20. The device of claim 16, wherein the anti-adhesion barrier layer comprises a first tier configured on the mesh structure and a second tier configured on the first tier, wherein the first tier is cured to a greater extent than the second tier.

21. The device of claim 16, wherein the anti-adhesion barrier layer comprises a first tier configured on the mesh structure and a second tier configured on the first tier, wherein the second tier is cured to a greater extent than the first tier.

22. The device of claim 16, wherein the anti-adhesion barrier layer is configured to provide controlled release of a therapeutic agent component.

23. The device of claim 16, wherein the anti-adhesion barrier layer comprises the cured fish oil in combination with at least one component selected from a group of components consisting of an uncured fish oil, a therapeutic agent component, a solvent, and a preservative.

24. The device of claim 16, wherein the heat-cured fish oil of the anti-adhesion barrier layer maintains anti-inflammatory properties.

25. A barrier layer device, comprising:
a biocompatible mesh structure; and
a barrier layer formed on at least a portion of the mesh structure; wherein the barrier layer comprises cured fish oil and uncured fish oil, wherein the cured fish oil is hydrolysable by lipase and comprises fatty acids and glycerides, wherein two or more of the fatty acids are cross-linked to each other by ester bonds in a substantially random configuration so that the barrier layer provides a biological oil barrier and a physical anti-adhesion barrier, and wherein the barrier layer degrades into non-inflammatory substances.

26. An implantable medical device, comprising:
a surgical mesh structure;
a bioabsorbable anti-adhesion barrier layer formed on at least a portion of the surgical mesh structure, wherein the barrier layer comprises a cured fish oil, wherein the fish oil comprises eicosapentaenoic acid and docosahexanoic acid, wherein the cured fish oil comprises fatty acids and glycerides, wherein the cured fish oil is hydrolysable by lipase and contains cross-linking between two or more fatty acids of the fish oil, wherein cross-linking in the anti-adhesion barrier layer is provided by ester and peroxide bonds, and wherein the anti-adhesion barrier layer is solid but flexible and serves as a physical barrier, and wherein the anti-adhesion barrier layer degrades into non-inflammatory substances comprising free fatty acids; and
a biological oil barrier layer supported by the anti-adhesion barrier layer, wherein the biological oil barrier layer comprises uncured fish oil.

* * * * *